US011834495B2

(12) United States Patent
Qiu et al.

(10) Patent No.: US 11,834,495 B2
(45) Date of Patent: Dec. 5, 2023

(54) MODIFIED-IGG ANTIBODIES THAT BIND TRANSFORMING GROWTH FACTOR-BETA1 WITH HIGH AFFINITY, AVIDITY AND SPECIFICITY

(71) Applicant: Genzyme Corporation, Cambridge, MA (US)

(72) Inventors: Huawei Qiu, Bridgewater, NJ (US); Julie Bird, Bridgewater, NJ (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 17/717,967

(22) Filed: Apr. 11, 2022

(65) Prior Publication Data

US 2022/0315649 A1 Oct. 6, 2022

Related U.S. Application Data

(62) Division of application No. 15/555,500, filed as application No. PCT/US2016/020780 on Mar. 3, 2016, now Pat. No. 11,325,970.

(60) Provisional application No. 62/128,149, filed on Mar. 4, 2015.

(51) Int. Cl.

| | |
|---|---|
| ***A61K 39/395*** | (2006.01) |
| ***C07K 16/22*** | (2006.01) |
| ***C12N 15/11*** | (2006.01) |

(52) U.S. Cl.

CPC .......... *C07K 16/22* (2013.01); *A61K 39/3955* (2013.01); *C12N 15/11* (2013.01); *C07K 2317/14* (2013.01); *C07K 2317/21* (2013.01); *C07K 2317/34* (2013.01); *C07K 2317/52* (2013.01); *C07K 2317/522* (2013.01); *C07K 2317/53* (2013.01); *C07K 2317/55* (2013.01); *C07K 2317/56* (2013.01); *C07K 2317/567* (2013.01); *C07K 2317/622* (2013.01); *C07K 2317/76* (2013.01); *C07K 2317/92* (2013.01); *C07K 2317/94* (2013.01)

(58) Field of Classification Search

CPC .. A61K 39/395; A61K 39/3955; C07K 16/22; C12N 15/11

See application file for complete search history.

(56) References Cited

U.S. PATENT DOCUMENTS

| | | | |
|---|---|---|---|
| 5,616,561 A | 4/1997 | Barcellos-Hoff | |
| 6,492,497 B1 * | 12/2002 | Thompson .............. | A61P 27/02 424/156.1 |
| 7,151,169 B2 | 12/2006 | Thompson et al. | |
| 7,619,069 B2 | 11/2009 | Davies et al. | |
| 8,048,421 B2 | 11/2011 | Kai et al. | |
| 8,632,774 B2 | 1/2014 | Misher et al. | |
| 10,508,146 B2 | 12/2019 | Qiu et al. | |
| 11,325,970 B2 | 5/2022 | Qiu et al. | |
| 11,325,971 B2 | 5/2022 | Qiu et al. | |
| 2002/0099179 A1 | 7/2002 | Jolliffe et al. | |
| 2008/0050375 A1 | 2/2008 | Davies et al. | |
| 2010/0174053 A1 | 7/2010 | Johnson et al. | |
| 2014/0072581 A1 | 3/2014 | Dixit et al. | |
| 2018/0044412 A1 | 2/2018 | Qiu et al. | |
| 2018/0222970 A1 | 8/2018 | Qiu et al. | |
| 2020/0131258 A1 | 4/2020 | Qiu et al. | |
| 2022/0363740 A1 | 11/2022 | Qiu et al. | |

FOREIGN PATENT DOCUMENTS

| | | |
|---|---|---|
| EP | 1486560 | 12/2004 |
| WO | WO 00/66631 A1 | 11/2000 |
| WO | WO 2004/098637 A1 | 11/2004 |
| WO | WO 2005/097832 A2 | 10/2005 |
| WO | WO 2006/036729 A3 | 4/2006 |
| WO | WO 2006/116002 A2 | 11/2006 |
| WO | WO 2007/109254 A1 | 2/2007 |
| WO | WO 2007/076391 A1 | 7/2007 |
| WO | WO 2008/060371 A1 | 5/2008 |
| WO | WO 2012/088461 A2 | 6/2012 |
| WO | WO 2012/135345 A1 | 10/2012 |
| WO | WO 2012/167143 A1 | 12/2012 |
| WO | WO 2014/164709 A2 | 10/2014 |

OTHER PUBLICATIONS

Aalberse et al., "lgG4 breaking the rules," *Immunol.* (2002) 105:9-19.

Alekperov, "Treatment of systemic scleroderma," *Russ. Open Med. J.* (2002) No. 22.

Armour et al., "Recombinant human IgG molecules lacking Fcgamma receptor I binding and monocyte triggering activities," *Eur J Immunol.* (1999) 29(8):2613-24.

Beck et al., "Strategies and challenges for the next generation of therapeutic antibodies," *Nature Reviews, Immunol.* (2010) 10:345-52.

Berry et al., "Substitution of cysteine for selenocysteine in type I iodothyronine deiodinase reduces the catalytic efficiency of the protein but enhances its translation," *Endocrinology* (1992) 131(4):1848-52.

Bird et al., "Single-Chain Antigen-Binding Proteins," *Science* (1988) 242:423-26.

(Continued)

*Primary Examiner* — Xiaozhen Xie

(74) *Attorney, Agent, or Firm* — Steptoe & Johnson LLC; Z. Ying Li; Mauricio Alvarez

(57) ABSTRACT

A modified IgG antibody binds and neutralizes TGFβ1 selectively and with high affinity and avidity. The modified IgG antibody comprises four polypeptide chains and may comprise modifications to the elbow regions of the polypeptide chains. The modified IgG antibody may comprise the same VH and VL domains or CDR regions as metelimumab. The modified IgG anti-body is useful in therapeutic and diagnostic applications.

11 Claims, 17 Drawing Sheets

Specification includes a Sequence Listing.

(56) References Cited

OTHER PUBLICATIONS

Border et al., "Suppression of experimental glomerulonephritis by antiserum against transforming growth factor β1," *Nature* (1990) 346:371-74.

Borsi et al., "Selective Targeting of Tumoral Vasculature: Comparison of Different Formats of an Antibody (L19) to the ED-B Domain of Fibronectin," *Int. J. Cancer*. (2002) 102:75-85.

Bujak et al., "Reformatting of scFv antibodies into the scFv-Fc format and their downstream purification," *Methods Mol Biol.* (2014) 1131:315-34.

Chen et al., "Enhancement and destruction of antibody function by somatic mutation: unequal occurrence is controlled by V gene combinatorial associations," *Embo J.* (1995) 14(12):2784-94.

Chiu et al., "Antibody Structure and Function: The Basis for Engineering Therapeutics," *Antibodies* (2019) 8(4):55.

Colman, "Effects of amino acid sequence changes on antibody-antigen interactions," Res Immunol. (1994) 145(1):33-36.

Correa et al., "Structure of a human IgA1 Fab fragment at 1.55   Å resolution: potential effect of the constant domains on antigen-affinity modulation," *Acta Crystallogr D Biol Crystallogr.* (2013) 69(3):388-97.

Waterhouse et al.: "Jalview Version 2—a multiple sequence alignment editor and analysis workbench," *Bioinformatics* (2009) 1189-191.

Datta-Mannan et al., "Humanized IgG1 variants with differential binding properties to the neonatal Fc receptor: relationship to pharmacokinetics in mice and primates," *Drug Metab Dispos.* (2007) 35:86-94.

Dondelinger et al., "Understanding the Significance and Implications of Antibody Numbering and Antigen-Binding Surface/Residue Definition", (2018) *Front Immunol.* 9:2278.

Fernandez-Quintero et al., "Suprisingly Fast Interface and Elbow Angle Dynamics of Antigen-Binding Fragments," *Front. Mol. Biosci.* (2020) 7:609088.

Gao et al., "Construction of Pichia pastoris expression vector for production of scFv-Fc fusion antibody against 40,000 adipocyte-specific plasma membrane protein," *Chin. J. Prev. Vet.* (2007) 27(3)376-86.

Gasser et al., "Antibody production with yeasts and filamentous fungi: on the road to large scale?" *Biotechnol Lett.* (2007) 29(2):201-12.

Giri et al., "Effect of antibody to transforming growth factor β on bleomycin induced accumulation of lung collagen in mice," *Thorax* (1993) 48:959-66.

Grütter et al., "A cytokine-neutralizing antibody as a structural mimetic of 2 receptor interactions," *Proc Natl Acad Sci USA.* (2008) 105(51):20251-6. doi: 10.1073/pnas.0807200106.

Harding et al., "The immunogenicity of humanized and fully human antibodies," *mAbs* (2010) 2(3):256-65.

Hieter et al., "Cloned human and mouse kappa immunoglobulin constant and J region genes conserve homology in functional segments," *Cell, Cell Press* (1980) 22(1):197-207.

Hinton et al., "Engineered Human IgG Antibodies with Longer Serum Half-lives in Primates," *Chem.* (2004) 279(8):6213-16.

Holliger et al., "Engineered antibody fragments and the rise of single domains," (2005) Nat Biotechnol. 23:1126-136.

Holmes et al., "Structural Consequences of Humanizing an Antibody," *J Immunol.* (1997) 158(5):2192-201.

Huston et al., "Protein engineering of antibody binding sites: Recovery of specific activity in an anti-digoxin single-chain Fv analogue produced in *Escherichia coli*," *Proc Natl Acad Sci USA.* (1988) 85(16):5879-83.

Idusogie et al., "Engineered Antibodies with Increased Activity to Recruit Complement," *J Immunol.* (2001) 166(4):2571-75.

Idusogie et al., "Mapping of the C1q Binding Site on Rituxan, a Chimeric Antibody with a Human IgG1 Fc," *J Immunol.* (2000) 164 (8):4178-84.

Ishii-Watabe et al., "Molecular Design of Therapeutic Monoclonal Antibodies," PDA J Pharm Sci Technol. (2014) 74(1):4-11.

Katsumoto et al., "The Pathogenesis of Systemic Sclerosis," *Annual Review of Pathology: Mechanisms of Disease* (2011) 6(1):509-37.

Knappik et al., "Fully synthetic human combinatorial antibody libraries (HuCAL) based on modular consensus frameworks and CDRs randomized with trinucleotides," *J Mol Biol.* (2000) 296(1):57-86.

Kussie et al., "A single engineered amino acid substitution changes antibody fine specificity," J Immunol. (1994) 152(1):146-52.

Labrijn et al., "Therapeutic IgG4 antibodies engage in Fab-arm exchange with endogenous human IgG4 in vivo," *Nature Biotechnol.* (2009) 27:767-71.

Landolfi et al., "The integrity of the ball-and-socket joint between V and C domains is essential for complete activity of a humanized antibody." *Am. J. Immunol.* (2001) 166(3):1748-54.

Lazar et al., "Engineered antibody Fc variants with enhanced effector function," *Proc. Natl Acad. Sci. USA.* (2006) 103:4005-10.

Lesk et al., "Elbow motion in the immunoglobulins involves a molecular ball-and-socket joint," *Nature* (1988) 335:188-190.

Logan et al., "Effects of transforming growth factor beta 1 on scar production in the injured central nervous system of the rat," *Eur J Neurosci.* (1994) 6:355-63.

Olafsen et al., "Antibody Vectors for Imaging," *Semin Nucl Med.* (2010) 40:167-181.

Peters et al., "Engineering an Improved IgG4 Molecule with Reduced Disulfide Bond Heterogeneity and Increased Fab Domain Thermal Stability," *J. Biol. Chem.* (2012) 287(29):24525-33.

Ponomarenko et al., "Role of [kappa]->[lambda] light-chain constant-domain switch in the structure and functionality of A17 reactibody," *Acta. Crystallogr. B. Struct.* (2014) 341(3):708-719.

Powers et al., "Expression of single-chain Fv-Fc fusions in Pichia pastoris," *J Immunol Methods.* (2001) 251:123-35.

Richards et al., "Optimization of antibody binding to FcgammaRIIa enhances macrophage phagocytosis of tumor cells," *Mol Cancer Ther* (2008) 7(8) 2517-27.

Rispens et al., "Dynamics of inter-heavy chain interactions in human immunoglobulin G (IgG) subclasses studied by kinetic Fab arm exchange," *J Biol Chem.* (2014) 289(9):6098-109.

Rudikoff et al., "Single amino acid substitution altering antigen-binding specificity," *Proc Natl Acad Sci USA.* (1982) 79(6):1979-83.

Ryan et al., "Antibody targeting of B-cell maturation antigen on malignant plasma cells," Mol Cancer Ther. (2007) 6(11):3009-18.

Sela-Culang et al., "The structural basis of antibody-antigen recognition," *Front Immunol.* (2013) 4:302.

Shah et al., "Neutralisation of TGF-beta 1 and TGF-beta 2 or exogenous addition of TGF-beta 3 to cutaneous rat wounds reduces scarring," *J. Cell Science.* (1995) 108:985-1002.

Shah et al., "Control of scarring in adult wounds by neutralising antibody to transforming growth factor β," *Lancet* (1992) 339(8787):213-4.

Shah et al., "Neutralising antibody to TGF-β1,2 reduces cutaneous scarring in adult rodents," *J Cell Sci.* (1994) 107(5):1137-57.

Shields et al., "High resolution mapping of the binding site on human IgG1 for Fc gamma RI, Fc gamma RII, Fc gamma RIII, and FcRn and design of IgG1 variants with improved binding to the Fc gamma R," *J. Biol. Chem.* (2001) 276:6591-604.

Stanfield et al., "Antibody Elbow Angles are Influenced by their Light Chain Class," *J. Mol. Biol.*(2006) 357(5):1566-74.

Steurer et al., "Ex vivo coating of islet cell allografts with murine CTLA4/Fc promotes graft tolerance," *J. Immunol.* 155:1165-74 (1995).

Strohl, "Optimization of Fc-mediated effector functions of monoclonal antibodies," *Curr Opin Biotechnol.* (2009) 20:685-91.

Torres et al., "The immunoglobulin constant region contributes to affinity and specificity," *Trends Immunol.* (2008) 29(2):91-97.

Vaccaro et al., "Engineering the Fc region of immunoglobulin G to modulate in vivo antibody levels," *Nat Biotechnol.* (2005) 23:1283-8.

Wahl et al., "Reversal of acute and chronic synovial inflammation by anti-transforming growth factor beta," *Exp. Medicine.* (1993) 177:225-230.

(56) References Cited

OTHER PUBLICATIONS

Yusakul et al., "Effect of linker length between variable domains of single chain variable fragment antibody against daidzin on its reactivity," *Biosci Biotechnol Biochem.* (2016) 80(7):1306-12.
Zhang et al., "Determination of Fab-Hinge Disulfide Connectivity in Structural Isoforms of a Recombinant Human Immunoglobulin G2 Antibody," *Anal. Chem.* (2010) 82:1090-99.

* cited by examiner

SDS Page Gel Electrophoresis of Purified IgG Mutants

Continued from Sheet 6 of 17

Continued from Sheet 7 of 17

Continued from Sheet 8 of 17

B.

SEQUENCE LISTING

<160> NUMBER OF SEQ ID NOS: 64

<210> SEQ ID NO 1
<211> LENGTH: 123
<212> TYPE: PRT
<213> ORGANISM: Homo sapiens

<400> SEQUENCE: 1

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Tyr Ser
            100                 105                 110

Trp Gly Gln Gly Thr Thr Val Thr Val Ser Ser
        115                 120
```

<210> SEQ ID NO 2
<211> LENGTH: 123
<212> TYPE: PRT
<213> ORGANISM: Homo sapiens

<400> SEQUENCE: 2

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
```

-continued

```
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Pro Ala Ser Pro Asp
            100                 105                 110

Trp Gly Gln Gly Thr Thr Val Thr Val Ser Ser
        115                 120


<210> SEQ ID NO 3
<211> LENGTH: 107
<212> TYPE: PRT
<213> ORGANISM: Homo sapiens

<400> SEQUENCE: 3

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Asp Asp
            20                  25                  30

Leu Gly Trp Tyr Gln Gln Lys Pro Gly Lys Ala Pro Ile Leu Leu Ile
        35                  40                  45

Tyr Gly Thr Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Leu Gln Asp Ser Asn Tyr Pro Leu
                85                  90                  95

Thr Phe Gly Gly Gly Thr Arg Leu Glu Ile Lys
            100                 105


<210> SEQ ID NO 4
<211> LENGTH: 107
<212> TYPE: PRT
<213> ORGANISM: Homo sapiens

<400> SEQUENCE: 4

Glu Ile Val Leu Thr Gln Ser Pro Ser Ser Leu Ser Ala Ser Val Gly
1               5                   10                  15

Asp Arg Val Thr Ile Thr Cys Arg Ser Ser Gln Gly Ile Gly Asp Asp
            20                  25                  30

Leu Gly Trp Tyr Gln Gln Lys Pro Gly Lys Ala Pro Ile Leu Leu Ile
        35                  40                  45

Tyr Gly Thr Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Leu Gln Asp Ser Asn Tyr Pro Leu
                85                  90                  95

Thr Phe Gly Gly Gly Thr Arg Leu Glu Ile Lys
            100                 105
```

<210> SEQ ID NO 5
<211> LENGTH: 22
<212> TYPE: PRT
<213> ORGANISM: Homo sapiens

<400> SEQUENCE: 5

Pro Lys Ser Cys Asp Lys Thr His Thr Cys Pro Pro Cys Pro Ala Pro
1               5                   10                  15

Glu Leu Leu Gly Gly Pro
            20

<210> SEQ ID NO 6
<211> LENGTH: 209
<212> TYPE: PRT
<213> ORGANISM: Homo sapiens

<400> SEQUENCE: 6

Ser Val Phe Leu Phe Pro Pro Lys Pro Lys Asp Thr Leu Met Ile Ser
1               5                   10                  15

Arg Thr Pro Glu Val Thr Cys Val Val Val Asp Val Ser His Glu Asp
            20                  25                  30

Pro Glu Val Lys Phe Asn Trp Tyr Val Asp Gly Val Glu Val His Asn
        35                  40                  45

Ala Lys Thr Lys Pro Arg Glu Glu Gln Tyr Asn Ser Thr Tyr Arg Val
    50                  55                  60

Val Ser Val Leu Thr Val Leu His Gln Asp Trp Leu Asn Gly Lys Glu
65                  70                  75                  80

Tyr Lys Cys Lys Val Ser Asn Lys Ala Leu Pro Ala Pro Ile Glu Lys
                85                  90                  95

Thr Ile Ser Lys Ala Lys Gly Gln Pro Arg Glu Pro Gln Val Tyr Thr
            100                 105                 110

Leu Pro Pro Ser Arg Asp Glu Leu Thr Lys Asn Gln Val Ser Leu Thr
        115                 120                 125

Cys Leu Val Lys Gly Phe Tyr Pro Ser Asp Ile Ala Val Glu Trp Glu
    130                 135                 140

Ser Asn Gly Gln Pro Glu Asn Asn Tyr Lys Thr Thr Pro Pro Val Leu
145                 150                 155                 160

Asp Ser Asp Gly Ser Phe Phe Leu Tyr Ser Lys Leu Thr Val Asp Lys
                165                 170                 175

Ser Arg Trp Gln Gln Gly Asn Val Phe Ser Cys Ser Val Met His Glu
            180                 185                 190

Ala Leu His Asn His Tyr Thr Gln Lys Ser Leu Ser Leu Ser Pro Gly
        195                 200                 205

Lys

<210> SEQ ID NO 7
<211> LENGTH: 5
<212> TYPE: PRT
<213> ORGANISM: Homo sapiens

<400> SEQUENCE: 7

Ser Tyr Gly Met His
1               5

<210> SEQ ID NO 8
<211> LENGTH: 17
<212> TYPE: PRT
<213> ORGANISM: Homo sapiens

<400> SEQUENCE: 8

Val Ile Ser Tyr Asp Gly Ser Ile Lys Tyr Tyr Ala Asp Ser Val Lys
1 5 10 15

Gly

<210> SEQ ID NO 9
<211> LENGTH: 14
<212> TYPE: PRT
<213> ORGANISM: Homo sapiens

<400> SEQUENCE: 9

Thr Gly Glu Tyr Ser Gly Tyr Asp Thr Ser Gly Val Glu Leu
1 5 10

<210> SEQ ID NO 10
<211> LENGTH: 14
<212> TYPE: PRT
<213> ORGANISM: Homo sapiens

<400> SEQUENCE: 10

Thr Gly Glu Tyr Ser Gly Tyr Asp Thr Asp Pro Gln Tyr Ser
1 5 10

<210> SEQ ID NO 11
<211> LENGTH: 14
<212> TYPE: PRT
<213> ORGANISM: Homo sapiens

<400> SEQUENCE: 11

Thr Gly Phe Tyr Ser Gly Tyr Asp Thr Pro Ala Ser Pro Asp
1 5 10

<210> SEQ ID NO 12
<211> LENGTH: 11
<212> TYPE: PRT
<213> ORGANISM: Homo sapiens

<400> SEQUENCE: 12

Arg Ala Ser Gln Gly Ile Gly Asp Asp Leu Gly
1 5 10

<210> SEQ ID NO 13
<211> LENGTH: 7
<212> TYPE: PRT
<213> ORGANISM: Homo sapiens

<400> SEQUENCE: 13

Gly Thr Ser Thr Leu Gln Ser
1 5

<210> SEQ ID NO 14
<211> LENGTH: 9
<212> TYPE: PRT
<213> ORGANISM: Homo sapiens

<400> SEQUENCE: 14

Leu Gln Asp Ser Asn Tyr Pro Leu Thr
1 5

<210> SEQ ID NO 15
<211> LENGTH: 14
<212> TYPE: PRT
<213> ORGANISM: Homo sapiens
<220> FEATURE:

<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (10)..(14)
<223> OTHER INFORMATION: Any amino acid

<400> SEQUENCE: 15

Thr Gly Xaa Tyr Ser Gly Tyr Asp Thr Xaa Xaa Xaa Xaa Xaa
1 5 10

<210> SEQ ID NO 16
<211> LENGTH: 213
<212> TYPE: PRT
<213> ORGANISM: Homo sapiens

<400> SEQUENCE: 16

Glu Trp Leu Thr Gln Ser Pro Ser Ser Leu Ser Ala Ser Val Gly Asp
1 5 10 15

Arg Val Thr Ile Thr Cys Arg Ala Ser Gln Gly Ile Gly Asp Asp Leu
20 25 30

Gly Trp Tyr Gln Gln Lys Pro Gly Lys Ala Pro Ile Leu Leu Ile Tyr
35 40 45

Gly Thr Ser Thr Leu Gln Ser Gly Val Pro Ser Arg Phe Ser Gly Ser
50 55 60

Gly Ser Gly Thr Asp Phe Thr Leu Thr Ile Asn Ser Leu Gln Pro Glu
65 70 75 80

Asp Phe Ala Thr Tyr Tyr Cys Leu Gln Asp Ser Asn Tyr Pro Leu Thr
85 90 95

Phe Gly Gly Gly Thr Arg Leu Glu Ile Lys Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

Val Gln Trp Lys Val Asp Asn Ala Leu Gln Ser Gly Asn Ser Gln Glu
145 150 155 160

Ser Val Thr Glu Gln Asp Ser Lys Asp Ser Thr Tyr Ser Leu Ser Ser
165 170 175

Thr Leu Thr Leu Ser Lys Ala Asp Tyr Glu Lys His Lys Val Tyr Ala
180 185 190

Cys Glu Val Thr His Gln Gly Leu Ser Ser Pro Val Thr Lys Ser Phe
195 200 205

Asn Arg Gly Glu Cys
210

<210> SEQ ID NO 17
<211> LENGTH: 450
<212> TYPE: PRT
<213> ORGANISM: Homo sapiens

<400> SEQUENCE: 17

Glu Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Glu Leu Glu Trp Val
35 40 45

-continued

```
Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Tyr Ser
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Ser Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450
```

<210> SEQ ID NO 18
<211> LENGTH: 450
<212> TYPE: PRT
<213> ORGANISM: Homo sapiens

<400> SEQUENCE: 18

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Tyr Ser
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450


<210> SEQ ID NO 19
<211> LENGTH: 245
<212> TYPE: PRT
<213> ORGANISM: Homo sapiens

<400> SEQUENCE: 19

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Tyr Ser
            100                 105                 110

Trp Gly Gln Gly Thr Thr Val Thr Val Ser Ser Ser Gly Gly Gly Ser
        115                 120                 125

Gly Gly Gly Gly Ser Gly Gly Gly Gly Ser Glu Ile Val Leu Thr Gln
    130                 135                 140

Ser Pro Ser Ser Leu Ser Ala Ser Val Gly Asp Arg Val Thr Ile Thr
145                 150                 155                 160

Cys Arg Ser Ser Gln Gly Ile Gly Asp Asp Leu Gly Trp Tyr Gln Gln
                165                 170                 175

Lys Pro Gly Lys Ala Pro Ile Leu Leu Ile Tyr Gly Thr Ser Thr Leu
            180                 185                 190

Gln Ser Gly Val Pro Ser Arg Phe Ser Gly Ser Gly Ser Gly Thr Asp
        195                 200                 205

Phe Thr Leu Thr Ile Asn Ser Leu Gln Pro Glu Asp Phe Ala Thr Tyr
    210                 215                 220

Tyr Cys Leu Gln Asp Ser Asn Tyr Pro Leu Thr Phe Gly Gly Gly Thr
225                 230                 235                 240

Arg Leu Glu Ile Lys
                245


<210> SEQ ID NO 20
<211> LENGTH: 112
<212> TYPE: PRT
<213> ORGANISM: Homo sapiens

<400> SEQUENCE: 20
```

```
Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110


<210> SEQ ID NO 21
<211> LENGTH: 8
<212> TYPE: PRT
<213> ORGANISM: Homo sapiens

<400> SEQUENCE: 21

Leu Glu Ile Lys Arg Thr Val Ala
1               5


<210> SEQ ID NO 22
<211> LENGTH: 9
<212> TYPE: PRT
<213> ORGANISM: Homo sapiens

<400> SEQUENCE: 22

Leu Glu Ile Lys Gly Arg Thr Val Ala
1               5


<210> SEQ ID NO 23
<211> LENGTH: 10
<212> TYPE: PRT
<213> ORGANISM: Homo sapiens

<400> SEQUENCE: 23

Leu Glu Ile Lys Gly Gly Arg Thr Val Ala
1               5                   10


<210> SEQ ID NO 24
<211> LENGTH: 11
<212> TYPE: PRT
<213> ORGANISM: Homo sapiens

<400> SEQUENCE: 24

Leu Glu Ile Lys Gly Gly Ser Arg Thr Val Ala
1               5                   10


<210> SEQ ID NO 25
<211> LENGTH: 12
<212> TYPE: PRT
<213> ORGANISM: Homo sapiens

<400> SEQUENCE: 25

Leu Glu Ile Lys Gly Gly Gly Ser Arg Thr Val Ala
1               5                   10


<210> SEQ ID NO 26
```

<211> LENGTH: 13
<212> TYPE: PRT
<213> ORGANISM: Homo sapiens

<400> SEQUENCE: 26

Leu Glu Ile Lys Gly Gly Gly Gly Ser Arg Thr Val Ala
1 5 10

<210> SEQ ID NO 27
<211> LENGTH: 702
<212> TYPE: DNA
<213> ORGANISM: Homo sapiens

<400> SEQUENCE: 27
atgggctggt cctgcatcat cctgtttctg gtggccacag ccaccggcgt gcacagcgag 60
atcgtgctga cacagagccc cagcagcctg tctgccagcg tgggcgacag agtgaccatc 120
acctgtagag ccagccaggg catcggcgac gacctgggat ggtatcagca gaagcctggc 180
aaggccccca tcctgctgat ctacggcacc agcacactgc agagcggcgt gccctccaga 240
ttttctggca gcggctccgg caccgacttc accctgacca tcaacagcct gcagcccgag 300
gacttcgcca cctactactg tctgcaagac agcaactacc ccctgacctt cggcggaggc 360
acccggctgg aaatcaagcg tacggtggcc gctccttccg tgttcatctt ccctccctcc 420
gacgagcagc tgaagtccgg caccgcctcc gtggtgtgtc tgctgaacaa cttctaccct 480
cgggaggcca aggtgcagtg gaaggtggac aacgccctgc agtccggcaa ctcccaggag 540
tccgtcaccg agcaggactc caaggacagc acctactccc tgtcctccac cctgaccctg 600
tccaaggccg actacgagaa gcacaaggtg tacgcctgtg aggtgaccca ccagggcctg 660
tccagccctg tgaccaagtc cttcaaccgg ggcgagtgct ga 702

<210> SEQ ID NO 28
<211> LENGTH: 31
<212> TYPE: DNA
<213> ORGANISM: Homo sapiens

<400> SEQUENCE: 28
ggctggaaat caagggccgt acggtggccg c 31

<210> SEQ ID NO 29
<211> LENGTH: 31
<212> TYPE: DNA
<213> ORGANISM: Homo sapiens

<400> SEQUENCE: 29
gcggccaccg tacggccctt gatttccagc c 31

<210> SEQ ID NO 30
<211> LENGTH: 34
<212> TYPE: DNA
<213> ORGANISM: Homo sapiens

<400> SEQUENCE: 30
ggctggaaat caagggcggc cgtacggtgg ccgc 34

<210> SEQ ID NO 31
<211> LENGTH: 34
<212> TYPE: DNA
<213> ORGANISM: Homo sapiens

<400> SEQUENCE: 31
gcggccaccg tacggccgcc cttgatttcc agcc 34

<210> SEQ ID NO 32
<211> LENGTH: 37
<212> TYPE: DNA
<213> ORGANISM: Homo sapiens

<400> SEQUENCE: 32
ggctggaaat caagggcggc agccgtacgg tggccgc 37

<210> SEQ ID NO 33
<211> LENGTH: 37
<212> TYPE: DNA
<213> ORGANISM: Homo sapiens

<400> SEQUENCE: 33
gcggccaccg tacggctgcc gcccttgatt tccagcc 37

<210> SEQ ID NO 34
<211> LENGTH: 40
<212> TYPE: DNA
<213> ORGANISM: Homo sapiens

<400> SEQUENCE: 34
ggctggaaat caagggcggc ggcagccgta cggtggccgc 40

<210> SEQ ID NO 35
<211> LENGTH: 40
<212> TYPE: DNA
<213> ORGANISM: Homo sapiens

<400> SEQUENCE: 35
gcggccaccg tacggctgcc gccgcccttg atttccagcc 40

<210> SEQ ID NO 36
<211> LENGTH: 43
<212> TYPE: DNA
<213> ORGANISM: Homo sapiens

<400> SEQUENCE: 36
ggctggaaat caagggcggc ggcggcagcc gtacggtggc cgc 43

<210> SEQ ID NO 37
<211> LENGTH: 43
<212> TYPE: DNA
<213> ORGANISM: Homo sapiens

<400> SEQUENCE: 37
gcggccaccg tacggctgcc gccgccgccc ttgatttcca gcc 43

<210> SEQ ID NO 38
<211> LENGTH: 214
<212> TYPE: PRT
<213> ORGANISM: Homo sapiens

<400> SEQUENCE: 38

```
Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Asp Asp
            20                  25                  30

Leu Gly Trp Tyr Gln Gln Lys Pro Gly Lys Ala Pro Ile Leu Leu Ile
        35                  40                  45
```

-continued

```
Tyr Gly Thr Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Leu Gln Asp Ser Asn Tyr Pro Leu
                85                  90                  95

Thr Phe Gly Gly Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 39
<211> LENGTH: 215
<212> TYPE: PRT
<213> ORGANISM: Homo sapiens

<400> SEQUENCE: 39

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Asp Asp
            20                  25                  30

Leu Gly Trp Tyr Gln Gln Lys Pro Gly Lys Ala Pro Ile Leu Leu Ile
        35                  40                  45

Tyr Gly Thr Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Leu Gln Asp Ser Asn Tyr Pro Leu
                85                  90                  95

Thr Phe Gly Gly Gly Thr Arg Leu Glu Ile Lys Gly Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205
```

```
Ser Phe Asn Arg Gly Glu Cys
    210                 215


<210> SEQ ID NO 40
<211> LENGTH: 216
<212> TYPE: PRT
<213> ORGANISM: Homo sapiens

<400> SEQUENCE: 40

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Asp Asp
            20                  25                  30

Leu Gly Trp Tyr Gln Gln Lys Pro Gly Lys Ala Pro Ile Leu Leu Ile
        35                  40                  45

Tyr Gly Thr Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Leu Gln Asp Ser Asn Tyr Pro Leu
                85                  90                  95

Thr Phe Gly Gly Gly Thr Arg Leu Glu Ile Lys Gly Gly Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215


<210> SEQ ID NO 41
<211> LENGTH: 217
<212> TYPE: PRT
<213> ORGANISM: Homo sapiens

<400> SEQUENCE: 41

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Asp Asp
            20                  25                  30

Leu Gly Trp Tyr Gln Gln Lys Pro Gly Lys Ala Pro Ile Leu Leu Ile
        35                  40                  45

Tyr Gly Thr Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Leu Gln Asp Ser Asn Tyr Pro Leu
                85                  90                  95
```

```
Thr Phe Gly Gly Gly Thr Arg Leu Glu Ile Lys Gly Gly Ser Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 42
<211> LENGTH: 218
<212> TYPE: PRT
<213> ORGANISM: Homo sapiens

<400> SEQUENCE: 42

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Asp Asp
            20                  25                  30

Leu Gly Trp Tyr Gln Gln Lys Pro Gly Lys Ala Pro Ile Leu Leu Ile
        35                  40                  45

Tyr Gly Thr Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Leu Gln Asp Ser Asn Tyr Pro Leu
                85                  90                  95

Thr Phe Gly Gly Gly Thr Arg Leu Glu Ile Lys Gly Gly Gly Ser Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 43
<211> LENGTH: 219
<212> TYPE: PRT
```

<213> ORGANISM: Homo sapiens

<400> SEQUENCE: 43

```
Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Asp Asp
            20                  25                  30

Leu Gly Trp Tyr Gln Gln Lys Pro Gly Lys Ala Pro Ile Leu Leu Ile
        35                  40                  45

Tyr Gly Thr Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Leu Gln Asp Ser Asn Tyr Pro Leu
                85                  90                  95

Thr Phe Gly Gly Gly Thr Arg Leu Glu Ile Lys Gly Gly Gly Gly Ser
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 44
<211> LENGTH: 8
<212> TYPE: PRT
<213> ORGANISM: Homo sapiens

<400> SEQUENCE: 44

```
Thr Val Thr Val Ser Ser Ala Ser
1               5
```

<210> SEQ ID NO 45
<211> LENGTH: 9
<212> TYPE: PRT
<213> ORGANISM: Homo sapiens

<400> SEQUENCE: 45

```
Thr Val Thr Val Ser Gly Ser Ala Ser
1               5
```

<210> SEQ ID NO 46
<211> LENGTH: 10
<212> TYPE: PRT
<213> ORGANISM: Homo sapiens

<400> SEQUENCE: 46

```
Thr Val Thr Val Ser Gly Gly Ser Ala Ser
1               5                   10
```

<210> SEQ ID NO 47
<211> LENGTH: 9
<212> TYPE: PRT
<213> ORGANISM: Homo sapiens

<400> SEQUENCE: 47

Thr Val Thr Val Ser Gly Gly Ser Ala
1 5

<210> SEQ ID NO 48
<211> LENGTH: 13
<212> TYPE: PRT
<213> ORGANISM: Homo sapiens

<400> SEQUENCE: 48

Thr Val Thr Val Ser Gly Gly Gly Gly Ser Ser Ala Ser
1 5 10

<210> SEQ ID NO 49
<211> LENGTH: 738
<212> TYPE: DNA
<213> ORGANISM: Homo sapiens

<400> SEQUENCE: 49
atgggctggt cctgcatcat cctgtttctg gtggccaccg ccaccggcgt gcactctgaa 60
gtgcagctgg tggaatctgg cggcggagtg gtgcagcctg gcagaagcct gagactgagc 120
tgtgccgcca gcggcttcac cttcagcagc tacggaatgc actgggtgcg ccaggcccct 180
ggcaaagaac tggaatgggt ggccgtgatc agctacgacg gcagcatcaa gtactacgcc 240
gacagcgtga agggccggtt caccatctcc cgggacaaca gcaagaacac cctgtacctg 300
cagatgaaca gcctgcgggc cgaggacacc gccgtgtact actgtgctag aaccggcgag 360
tacagcggct acgacaccga ccctcagtac tcttggggcc agggcaccac cgtgacagtg 420
tctagcgcca gcaccaaggg cccaagcgtg ttccctctgg ccccttgcag cagaagcacc 480
agcgaatcta cagccgccct gggctgcctc gtgaaggact actttcccga gcccgtgaca 540
gtgtcctgga actctggcgc cctgaccagc ggagtgcata cctttccagc cgtgctgcag 600
agcagcggcc tgtactctct gagcagcgtc gtgactgtgc ccagcagctc tctgggcacc 660
aagacctaca cctgtaacgt ggaccacaag cccagcaaca ccaaggtgga caagagagtg 720
catcaccacc accatcac 738

<210> SEQ ID NO 50
<211> LENGTH: 29
<212> TYPE: DNA
<213> ORGANISM: Homo sapiens

<400> SEQUENCE: 50
ccaccgtgac agtgtctggc agcgccagc 29

<210> SEQ ID NO 51
<211> LENGTH: 29
<212> TYPE: DNA
<213> ORGANISM: Homo sapiens

<400> SEQUENCE: 51
gctggcgctg ccagacactg tcacggtgg 29

<210> SEQ ID NO 52
<211> LENGTH: 32

<212> TYPE: DNA
<213> ORGANISM: Homo sapiens

<400> SEQUENCE: 52
ccaccgtgac agtgtctggc ggcagcgcca gc 32

<210> SEQ ID NO 53
<211> LENGTH: 32
<212> TYPE: DNA
<213> ORGANISM: Homo sapiens

<400> SEQUENCE: 53
gctggcgctg ccgccagaca ctgtcacggt gg 32

<210> SEQ ID NO 54
<211> LENGTH: 44
<212> TYPE: DNA
<213> ORGANISM: Homo sapiens

<400> SEQUENCE: 54
caccaccgtg acagtgtctg gcggcggcgg cagcagcgcc agca 44

<210> SEQ ID NO 55
<211> LENGTH: 44
<212> TYPE: DNA
<213> ORGANISM: Homo sapiens

<400> SEQUENCE: 55
tgctggcgct gctgccgccg ccgccagaca ctgtcacggt ggtg 44

<210> SEQ ID NO 56
<211> LENGTH: 454
<212> TYPE: PRT
<213> ORGANISM: Homo sapiens

<400> SEQUENCE: 56

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Tyr Ser
            100                 105                 110

Trp Gly Gln Gly Thr Thr Val Thr Val Ser Gly Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val

```
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450


<210> SEQ ID NO 57
<211> LENGTH: 453
<212> TYPE: PRT
<213> ORGANISM: Homo sapiens

<400> SEQUENCE: 57

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Thr Gly Glu Tyr Ser Gly Tyr Asp Thr Asp Pro Gln Tyr Ser
            100                 105                 110

Trp Gly Gln Gly Thr Thr Val Thr Val Ser Gly Gly Ser Ala Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 58
<211> LENGTH: 458
<212> TYPE: PRT
<213> ORGANISM: Homo sapiens

<400> SEQUENCE: 58

```
Glu Val Gln Leu Val Glu Ser Gly Gly Gly Val Val Gln Pro Gly Arg
1               5                   10                  15
```

-continued

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Tyr Ser
            100                 105                 110

Trp Gly Gln Gly Thr Thr Val Thr Val Ser Gly Gly Gly Gly Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430
```

-continued

```
Val Phe Ser Cys Ser Val Met His Glu Ala Leu His Asn His Tyr Thr
        435                 440                 445

Gln Lys Ser Leu Ser Leu Ser Pro Gly Lys
    450                 455


<210> SEQ ID NO 59
<211> LENGTH: 35
<212> TYPE: DNA
<213> ORGANISM: Homo sapiens

<400> SEQUENCE: 59

caccaccgtg acagtgtctg gcggcagcgc cagca                                35


<210> SEQ ID NO 60
<211> LENGTH: 35
<212> TYPE: DNA
<213> ORGANISM: Homo sapiens

<400> SEQUENCE: 60

tgctggcgct gccgccagac actgtcacgg tggtg                                35


<210> SEQ ID NO 61
<211> LENGTH: 455
<212> TYPE: PRT
<213> ORGANISM: Homo sapiens

<400> SEQUENCE: 61

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Tyr Ser
            100                 105                 110

Trp Gly Gln Gly Thr Thr Val Thr Val Ser Gly Gly Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240
```

```
Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455
```

<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence: Synthetic linker

<400> SEQUENCE: 62

```
Gly Gly Gly Ser
1
```

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic linker

<400> SEQUENCE: 63

```
Gly Gly Gly Gly Ser
1               5
```

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic linker -continued

<400> SEQUENCE: 64

```
Gly Gly Gly Gly Ser Gly Gly Gly Gly Ser Gly Gly Gly Gly Ser
1               5                   10                  15
```

MODIFIED-IGG ANTIBODIES THAT BIND TRANSFORMING GROWTH FACTOR-BETA1 WITH HIGH AFFINITY, AVIDITY AND SPECIFICITY

RELATED APPLICATIONS

This patent application is a divisional of U.S. patent application Ser. No. 15/555,500, filed Sep. 2, 2017, now U.S. Pat. No. 11,325,970, which claims the benefit of National Stage under 35 U.S.C. § 371 of International Application No. PCT/US2016/020780, filed Mar. 3, 2016, which claims the benefit of U.S. Provisional Patent Application 62/128,149, filed Mar. 4, 2015. The disclosures of both of the International Application and the Provisional Application are incorporated herein by reference in their entirety.

SEQUENCE LISTING

A sequence listing associated with this application is being submitted electronically via EFS-Web in text format, and is hereby incorporated in its entirety into the specification. The name of the text file containing the Sequence Listing is 022548_D1016 SL.txt. The text file was created on Apr. 10, 2022 and is 55,283 in size.

BACKGROUND OF THE INVENTION

Field of the Invention

Modified-IgG antibodies, each comprising a first, a second, a third and a fourth polypeptide chain, which exhibit high affinity and avidity to Transforming Growth Factor-β1 (TGFβ1) but not to TGFβ2 or TGFβ3. Compositions comprising the modified-IgG antibodies and methods of using the same for treatment of diseases involving TGFβ1 activity are provided.

Many severe diseases are linked to malfunctions of the TGFβ-induced signaling pathway. For instance, an increased tissue level of TGFβ is believed to be a factor in the development of idiopathic pulmonary fibrosis and myocardial fibrosis. Furthermore, high local tissue levels of TGFβ may allow the maintenance and progression of some types of cancer cells. Down-regulation of TGFβ signaling therefore may reduce the viability of such tumor cells.

TGFβ isoforms are ~25 kDa homodimeric molecules with a similar structural framework in which two monomers are covalently linked via a disulfide bridge. The mammalian isoforms share a sequence identity of 70-82%, but have non-overlapping activities in vascular development and the regulation of immune cell function. Three TGFβ isoforms have been reported in humans: TGFβ1, TGFβ2, and TGFβ3 (Swiss Prot accession numbers P01137, P08112, and P10600, respectively). TGFβ1 and TGFβ3 trigger a cellular signaling cascade upon binding to the extracellular domains of two transmembrane receptors, known as TGFβ receptor types I and II. TGFβ2 may bind to TGFβ receptor types I and II, as well as TGFβ receptor type III.

Antibodies that can bind human TGFβ1, TGFβ2, and TGFβ3 have been tested for clinical use. For instance, Grater et al. disclosed GC1008, a human IgG4 monoclonal antibody (Mab; i.e., GC1008) in clinical development for treating malignancy and fibrotic diseases. *Proc. Nat'l Acad. Sci. USA* 105(51): 20251-56 (2008). GC1008 is a "pan-specific" TGFβ neutralizing antibody, because it can neutralize all three human TGFβ isoforms. Antibodies that selectively neutralize TGFβ1 are disclosed, for example, in U.S. Pat. Nos. 6,492,497 and 7,151,169, which are incorporated by reference into this disclosure. Metelimumab, also known as CAT192 (IgG4), is a human IgG4 monoclonal antibody that selectively neutralizes TGF-β1. See e.g., U.S. Pat. No. 6,492,497. Metelimumab was tested for the treatment of diffuse cutaneous systemic sclerosis, also known as scleroderma, but demonstrated insufficient efficacy.

BRIEF SUMMARY OF THE INVENTION

The present disclosure provides TGFβ1-binding modified-IgG antibodies that are capable of selectively binding and neutralizing human TGFβ1. The disclosed modified-IgG antibodies are derived from metelimumab. The VH and VL domains of the modified-IgG antibodies exhibit a TGFβ1-binding affinity and avidity and TGFβ1 neutralizing capability similar to those of metelimumab. In many cases, the disclosed antibodies offer improved affinity, avidity and neutralization capacity over metelimumab. In one embodiment, the modified-IgG antibodies contain two polypeptide chains each comprising a VL domain linked to a CL domain, and two polypeptide chains each comprising a VH domain linked to a CH1 domain, a hinge and a Fc region.

The modified-IgG antibodies of the present invention comprise a variable domain that is capable of binding TGFβ1. In another embodiment, the disclosed modified-IgG antibodies comprise a binding protein which exhibits a Kd for human TGFβ1 at least about 50% lower than the Kd of the same binding protein for human TGFβ2, as measured by surface plasmon resonance.

In another embodiment, the present invention is directed to an isolated binding protein comprising a variable domain that is capable of binding TGFβ1, wherein the binding protein exhibits a Kd for human TGFβ1 at least about 50% lower than the Kd of the same binding protein for human TGFβ3, as measured by surface plasmon resonance.

In a further embodiment, the present invention is directed to an isolated binding protein comprising a variable domain that is capable of binding TGFβ1, wherein the binding protein exhibits a Kd for human TGFβ1 at least about 50% lower than the Kd of the same binding protein for human TGFβ2, and at least about 50% lower than the Kd of the same binding protein for human TGFβ3, as measured by surface plasmon resonance.

In a further embodiment, the present invention is directed to an isolated binding protein that binds TGFβ1, wherein the binding protein comprises a first polypeptide chain, a second polypeptide chain, a third polypeptide chain and a fourth polypeptide chain. In one aspect, the first and second polypeptide chains have the formula of, from N-terminal to C-terminal:

(VL domain)-(linker1)$_m$-(CL domain), wherein the VL domain comprises a variable light complementarity determining region 1 (LCDR1), a variable light complementarity determining region 2 (LCDR2), and a variable light complementarity determining region 3 (LCDR3), and wherein m is 1, and wherein the linker1 comprises a peptide having the sequence of Leucine-Glutamic acid-Isoleucine-Lysine-$X_p$-$Y_q$-Zr-Arginine-Threonine-Valine-Alanine, X, Y and Z being independently an amino acid selected from the group consisting of Serine, Glycine, Alanine, Valine, Leucine, Isoleucine, and Threonine, and each of p, q and r being independently an integer from 0 to 5. In another aspect, the third and fourth polypeptide chains have the formula of, from N-terminal to C-terminal:

(VH domain)-(linker2)$_n$-(CH1 domain)-(hinge)s-(Fc region), wherein the VH domain comprises a variable heavy complementarity determining region 1 (HCDR1), a variable heavy complementarity determining region 2 (HCDR2), and a variable heavy complementarity determining region 3 (HCDR3); and wherein n is 0 or 1 and s is 0 or 1. In another aspect, linker2 may contain a peptide having the sequence of Threonine-Valine-Serine-$A_d$-$B_e$-$C_f$-Serine-Alanine-Serine-Threonine, A, B and C being independently an amino acid selected from the group consisting of Serine, Glycine, Alanine, Valine, Leucine, Isoleucine, and Threonine, and each of d, e and f being independently an integer from 0 to 5.

In one aspect, linker2 may contain a sequence selected from the group consisting of SEQ ID No. 45, SEQ ID No. 46, SEQ ID No. 47, and SEQ ID No. 48.

In one aspect, the HCDR1 may have the amino acid sequence of SEQ ID No. 7, The HCDR2 may have the amino acid sequence of SEQ ID No. 8, and the HCDR3 may have the amino acid sequence of SEQ ID No. 9, SEQ ID No. 10, SEQ ID No. 11, or SEQ ID No. 15.

The framework regions of the VH domain may be selected from a variable heavy germline sequence. The VH domain may be selected, for example, from the human VH domain sequences set forth in SEQ ID No. 1 or SEQ ID No. 2, or a variant thereof having modifications of up to five amino acids.

The VL domain of the disclosed binding protein may comprise a variable light complementarity determining region 1 (LCDR1), a variable light complementarity determining region 2 (LCDR2), and a variable light complementarity determining region 3 (LCDR3). In one aspect, the LCDR1 may have the amino acid sequence of SEQ ID No. 12, the LCDR2 may have the amino acid sequence of SEQ ID No. 13, and the LCDR3 may have the amino acid sequence of SEQ ID No. 14.

The framework regions of the VL domain may be selected from a variable lambda or kappa germline sequence. The VL domain may be selected, for example, from the human Vκ domain sequences set forth in SEQ ID No. 3 or SEQ ID No. 4, or a variant thereof having modifications of up to four amino acids. In one embodiment, each polypeptide of the dimer may comprise the VH domain set forth in SEQ ID NO: 1 and the Vκ domain set forth in SEQ ID No. 3, which are the VH and VL domains present in metelimumab, respectively.

In another embodiment, the Fc region is connected to the CH1 domain by a hinge. The hinge may comprise amino acid sequences derived from a human IgG1 or IgG4 hinge region. For example, the hinge may comprise the amino acid sequence PKSCDKTHTCPPCPAPELLGGP (SEQ ID No. 5), or a variant thereof having up to five amino acid modifications. In one embodiment, the hinge length may vary from 1-15 amino acids.

In another embodiment, site-directed mutagenesis is performed on CAT192 Fab elbow regions to improve TGFβ1 binding affinity. One to five amino acids (G, GG, GGS, GGGS (SEQ ID NO: 62) and GGGGS (SEQ ID NO: 63)) are inserted to the light chain elbow region to increase the flexibility of the hinge that may be required to present a functional binding paratope from the two chains. Conditioned media from an Expi293 transfection show good expression and significant improvement in binding to TGFβ1 by Octet. The mutants are purified by Ni-NTA and high TGFβ binding affinities are confirmed using Biacore. The CAT192 mutants with 1 to five amino acids inserted into the LC elbow region re-gain the high affinity binding of scFv to TGFβ1. These engineered elbow insertion mutants also retain isoform-selectivity and may serve as TGFβ1 specific antagonists.

In another aspect, the VH domain may contain a variable heavy complementarity determining region 1 (HCDR1) having the amino acid sequence of SEQ ID No. 7, a variable heavy complementarity determining region 2 (HCDR2) having the amino acid sequence of SEQ ID No. 8, and a variable heavy complementarity determining region 3 (HCDR3) having the amino acid sequence selected from the group consisting of SEQ ID No. 9, SEQ ID No. 10, SEQ ID No. 11, and SEQ ID No. 15.

In another aspect, the VL domain may contain a variable light complementarity determining region 1 (LCDR1) having the amino acid sequence of SEQ ID No. 12, a variable light complementarity determining region 2 (LCDR2) having the amino acid sequence of SEQ ID No. 13, and a variable light complementarity determining region 3 (LCDR3) having the amino acid sequence of SEQ ID No. 14.

In another aspect, linker1 may contain a peptide having the sequence of Leucine-Glutamic acid-Isoleucine-Lysine-$X_p$-$Y_q$-$Z_r$-Arginine-Threonine-Valine-Alanine, wherein X, Y and Z is independently an amino acid selected from the group consisting of Serine, Glycine, Alanine, Valine, Leucine, Isoleucine, and Threonine, and each of p, q and r is independently an integer from 0 to 5. In another aspect, each of X, Y and Z is preferably Serine and Glycine. In another aspect, each of p, q and r is 1. In another aspect, p is 0 and each of q and r is 1. In another aspect, p is 1 and each of q and r is 0. In another aspect, p is 2 and each of q and r is 1. In another aspect, p is 1 and each of q and r is 2.

In one embodiment, linker1 may contain a sequence selected from the group consisting of SEQ ID No. 22, SEQ ID No. 23, SEQ ID No. 24, SEQ ID No. 25, and SEQ ID No. 26, each of which is a mutated form derived from SEQ ID No. 21. In another embodiment, the first polypeptide chain contains a sequence selected from the group consisting of SEQ ID No. 39, SEQ ID No. 40, and SEQ ID No. 41, each of which is a mutated form derived from the light chain of CAT192 IgG1 (SEQ ID No. 38).

In another aspect, linker1 and linker2 may be each independently as described for linker1 above. In this aspect, linker2 may contain a peptide having the sequence of Leucine-Glutamic acid-Isoleucine-Lysine-$A_d$-$B_e$-$C_f$-Arginine-Threonine-Valine-Alanine, wherein A, B and C is independently an amino acid selected from the group consisting of Serine, Glycine, Alanine, Valine, Leucine, Isoleucine, and Threonine, and each of d, e and f is independently an integer from 0 to 5. In another aspect, each of A, B and C is preferably Serine and Glycine. In another aspect, each of d, e and f is 1. In another aspect, d is 0 and each of e and f is 1. In another aspect, d is 1 and each of e and f is 0. In another aspect, d is 2 and each of e and f is 1. In another aspect, d is 1 and each of e and f is 2.

In another embodiment, the linker2 may contain a sequence selected from the group consisting SEQ ID No. 22, SEQ ID No. 23, SEQ ID No. 24, SEQ ID No. 25, and SEQ ID No. 26, each of which is a mutated form derived from SEQ ID No. 21. In another embodiment, the first polypeptide chain contains a sequence selected from the group consisting of SEQ ID No. 39, SEQ ID No. 40, and SEQ ID No. 41, each of which is a mutated form derived from the light chain of CAT192 IgG1 (SEQ ID No. 38).

In another embodiment, the disclosed TGFβ1-binding Fab or IgG molecules selectively binds TGFβ1, but does not bind TGFβ2 or TGFβ3 to a significant extent.

In another embodiment, an isolated polynucleotide is disclosed which may comprise a nucleotide sequence encoding the modified IgG antibodies disclosed herein. The isolated polynucleotide may be a cDNA, a recombinant DNA or a synthetic DNA. A host cell may comprise the isolated nucleic acid. The host cell may be a human cell, such as a Human Embryonic Kidney 293 (HEK293) cell and cell lines derived therefrom, or it may be a Chinese Hamster Ovary (CHO) cell. A method of making the modified IgG antibodies may include culturing the host cell under suitable conditions to produce the modified IgG antibodies. The modified IgG antibodies may be purified. The degree of purity may be 90%, 95%, 99%, 99.5% or more.

In certain embodiments, the modified IgG antibodies of the present invention may be an element of a composition. The composition may be a pharmaceutical composition. The pharmaceutical composition may comprise a therapeutically effective amount of the modified IgG antibodies. The composition may further comprise one or more biologically active components, excipients, or diluents.

Also provided is a method of treating a disease or condition resulting directly or indirectly from TGFβ1 activity in a human comprising administering a pharmaceutical composition comprising a therapeutically effective amount of the modified IgG antibodies. The disease or condition may be selected from the group consisting of a fibrotic disease, cancer, or an immune-mediated disease, e.g., diffuse cutaneous systemic sclerosis, bone remodeling disease, kidney disease and/or a combination thereof. The modified IgG antibodies may be used in the manufacture of a medicament for treatment of a disease or disorder selected from the group consisting of a fibrotic disease, cancer, or an immune-mediated disease, e.g., diffuse cutaneous systemic sclerosis, bone remodeling disease, kidney disease and/or a combination thereof. The treatment of the disease or disorder may comprise neutralizing TGFβ1 or inhibiting TGFβ1 signaling. The treatment of the disease or disorder may comprise inhibiting TGFβ1-mediated fibronectin production, vascular endothelial growth factor (VEGF) production, epithelial cell proliferation, endothelial cell proliferation, smooth muscle cell proliferation, and/or immunosuppression. The treatment of the disease or disorder may comprise increasing natural killer cell activity.

BRIEF DESCRIPTION OF THE SEVERAL VIEWS OF THE DRAWING(S)

The drawings presented herein are for purpose of illustration and are not to be used to limit the scope of the present invention.

DETAILED DESCRIPTION OF THE INVENTION

Figure 1:
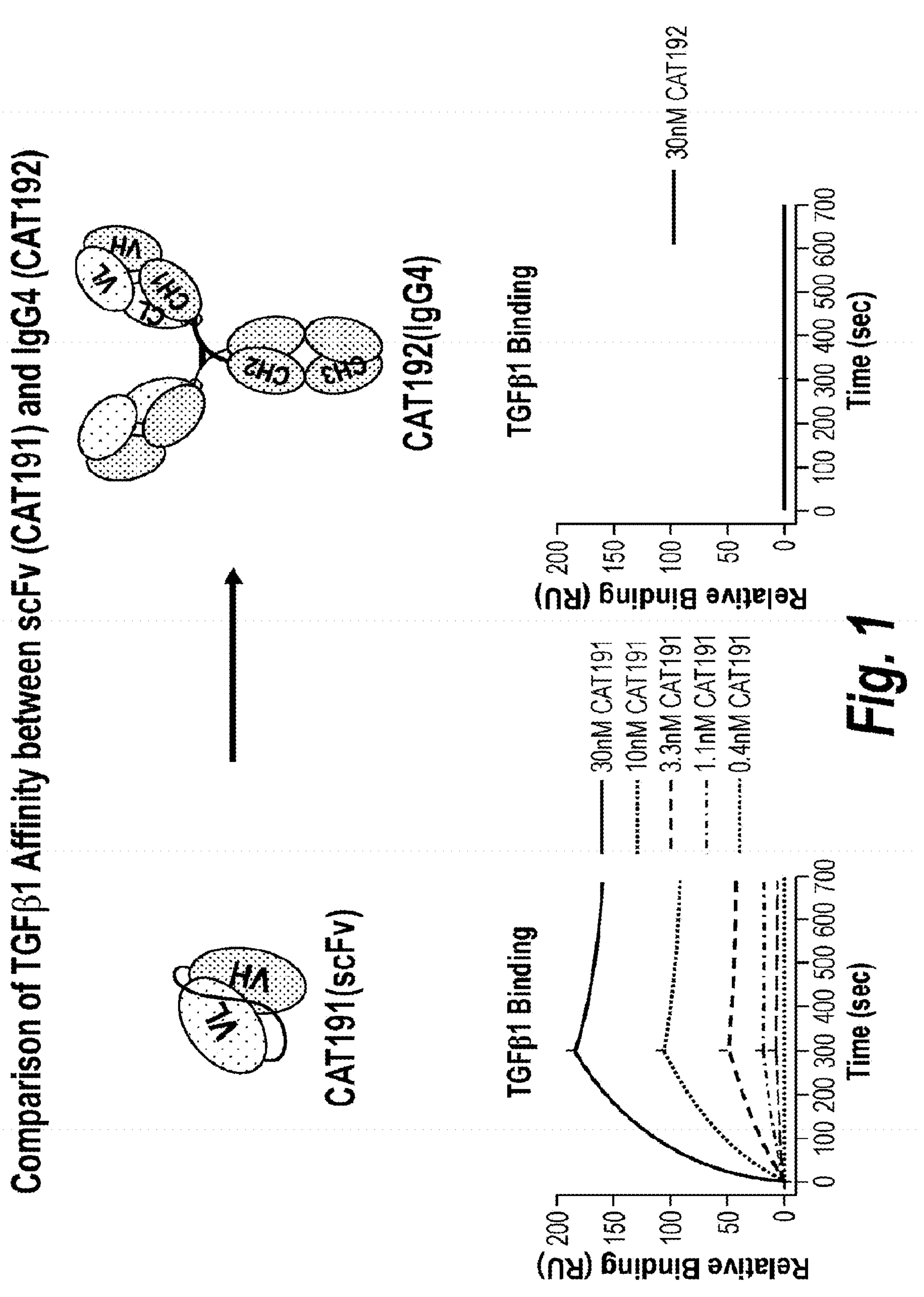
FIG. 1 depicts the results of a Biacore TGFβ1 binding assay which showed the loss of affinity when the scFv (CAT191) was converted into a full length IgG4 (CAT192) molecule.
Figure 2:
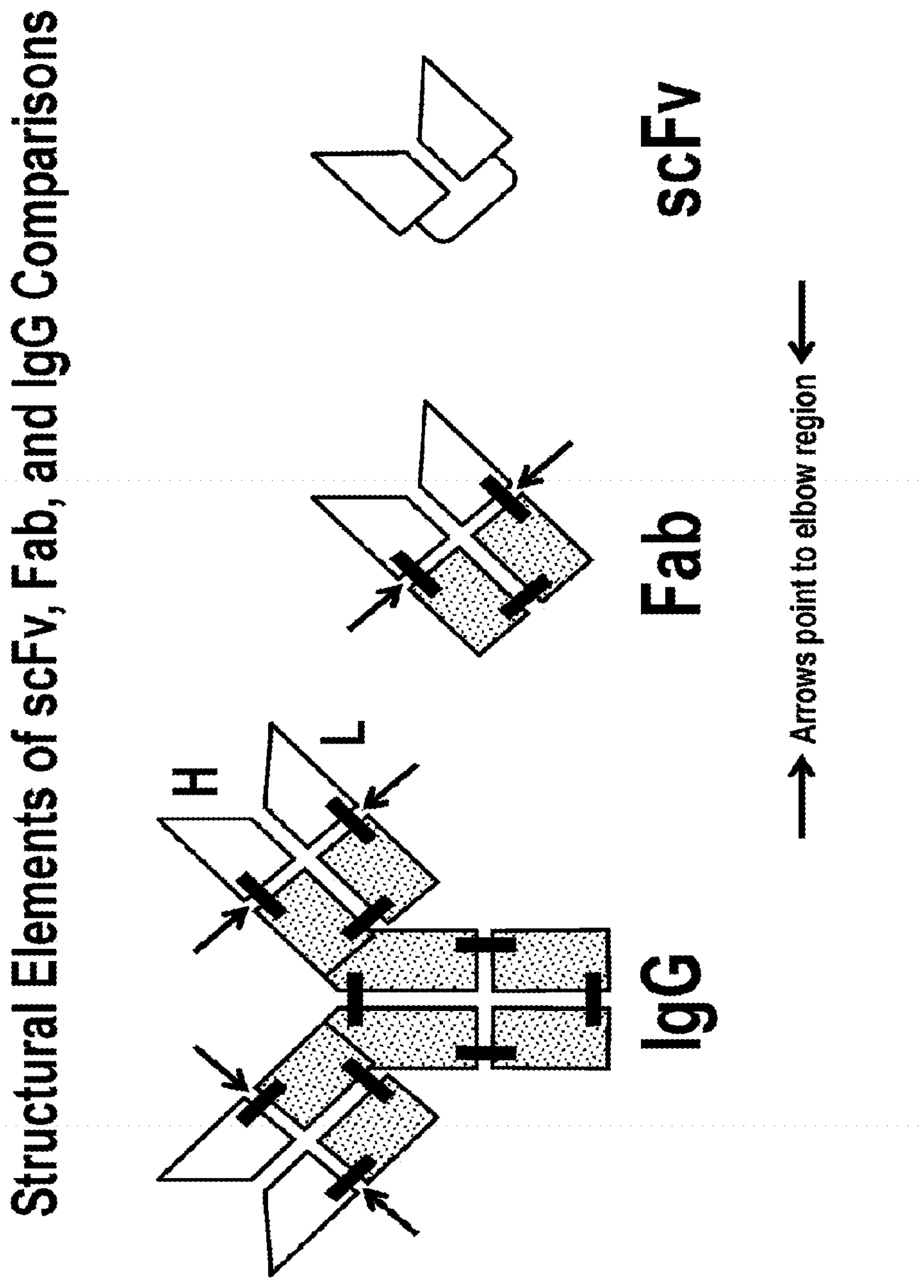
FIG. 2 depicts structural elements of a scFv, a Fab, an IgG molecule, and the elbow regions that were engineered to restore affinity.

The disclosed modified IgG antibodies bind and neutralize TGFβ1 selectively and with high affinity and avidity. The modified IgG antibodies may be composed of the same VH and VL domains as in metelimumab. The modified IgG antibodies advantageously show greater efficacy in neutralizing TGFβ1 than when the variable domains are used in other formats.

As used herein, a first element "and/or" a second element means a specific disclosure of the first or second element separately, or the first and second elements in combination. The singular forms "a," "an," and "the" include plural referents unless the context clearly dictates otherwise.

An "isolated" polynucleotide (or nucleic acid) or protein is removed and/or altered from its natural form using genetic engineering technologies. A "purified" nucleic acid or protein may be substantially pure, e.g., at least 90% pure, or in homogeneous form.

"Selective binding", or "binding selectively" to human TGFβ1, means that the binding protein (e.g., scFv-Fc dimer) is capable of binding human TGFβ1 with a higher affinity than binding to human TGFβ2 or human TGFβ3, e.g., with a dissociation constant with human TGFβ1 at least 50% lower than its dissociation constant with human TGFβ2 or human TGFβ3, as measured by surface plasmon resonance.

In one embodiment, the present modified IgG antibodies' variable domains comprise complementarity determining regions (CDRs) from the CDRs disclosed in U.S. Pat. No. 6,492,497 (e.g., SEQ ID Nos. 11-19 of U.S. Pat. No. 6,492,497), incorporated herein by reference. The CDR regions are listed below:

| | | |
|---|---|---|
| HCDR1 | SYMGH | SEQ ID No. 7 |
| HCDR2 | VISYDGSIKYYADSVKG | SEQ ID No. 8 |
| HCDR3 | TGEYSGYDTSGVEL<br>TGEYSGYDTDPQYS<br>TGFYSGYDTPASPD | SEQ ID No. 9<br>SEQ ID No. 10<br>SEQ ID No. 11 |
| LCDR1 | RASQGIGDDLG | SEQ ID No. 12 |
| LCDR2 | GTSTLQS | SEQ ID No. 13 |
| LCDR3 | LQDSNYPLT | SEQ ID No. 14 |

Surprisingly, a consensus HCDR3 binding motif is revealed, having the sequence:

| | | |
|---|---|---|
| HCDR3 | $TGX_1YSGYDTX_2X_3X_4X_5X_6$ | SEQ ID No. 15 |

Wherein: $X_1$ may be any amino acid (preferably E, or F), or absent, $X_2$ may be any amino acid (preferably S, D, or P), or absent, $X_3$ may be any amino acid (preferably G, P, or A), or absent, $X_4$ may be any amino acid (preferably V, Q, or S), or absent, $X_5$ may be any amino acid (preferably E, Y, or P), or absent, $X_6$ may be any amino acid (preferably L, S, or D), or absent.

In one embodiment, the VH domain of the disclosed modified antibodies comprises a HCDR1 having the sequence of SEQ ID No. 7, a HCDR2 having the sequence of SEQ ID No. 8, and a HCDR3 having a sequence selected from the group consisting of SEQ ID No. 9, SEQ ID No. 10, SEQ ID No. 11, and SEQ ID No. 15. The CDR sequences may be separated by anywhere from one to four framework regions, in order from the N-terminal: FW1-CDR1-FW2-CDR2-FW3-CDR3-FW4. The framework regions of the VH domain may be selected from a variable heavy germline sequence. In one embodiment, the FW region sequences may be selected from the same human variable heavy germline sequence. The framework regions of the VL domain may be selected from a variable lambda or kappa germline sequence, e.g., from the same human variable lambda or kappa germline sequence. At present, about 40 variable heavy germline sequences are known in the art, as are about 40 variable kappa germline sequences and about 30 variable lambda germline sequences, e.g., $V_H3$, Vκ1, $V_H$ 1-69, and $V_H$ 1-e.

In another embodiment, composite VH or VL domains may be generated by using the CDR sequences disclosed herein. For example, crystal structures of the VH or VL domains may be used as a guidance to generate composite domain using CDR sequences from one antibody and using the germline FW regions from another antibody. More details can be found in U.S. Patent Application Publication No. 20020099179; and Homes and Foote, J Immunol. 1997 Mar. 1; 158(5):2192-201, both of which are hereby incorporated into this disclosure by reference.

The present modified IgG antibodies may be composed of the same VH and VL domains as in metelimumab, having the sequences set forth in SEQ ID No. 1 and SEQ ID No. 3, respectively. The VH domain may be replaced by the VH domain having the sequences set forth in SEQ ID No. 2; the VL domain may be replaced by the VL domain having the sequences set forth in SEQ ID No. 4. These VH and VL domains are disclosed in U.S. Pat. No. 6,492,497 (e.g., SEQ ID Nos. 4, 6, 8, and 10 of U.S. Pat. No. 6,492,497), incorporated herein by reference.

A "variable domain" (VD) refers to a hypervariable binding domain of an immunoglobulin, or a ligand binding domain of a receptor, involved in antigen/ligand binding as is known by persons skilled in the art. Variable domains are routinely referred to by their location or origin within an immunoglobulin; e.g., variable domains of the light chain of an immunoglobulin (VL), variable domains of the heavy chain of an immunoglobulin (VH), variable domains of the heavy chain of a camelid immunoglobulin (VHH).

A "variant" variable domain comprises amino acid additions, substitutions, and/or deletions, compared to the reference sequence. A "variant" of the VH or VL domains may have up to four such amino acid modifications. For example, one of the two domains may comprise an amino acid substitution, while the other domain is unmodified, or both of the domains may comprise amino acid substitutions. Modifications that add or delete amino acid residues may be made at the N-terminus or C-terminus of the VH or VL domain. For example, the N-terminal residue of the VH domain may be deleted.

For purpose of this disclosure, the terms "between," "from," "to," and "at least" are inclusive. For example, an integer "from 0 to 5" means any integer equal to or greater than 0 but equal to or smaller than 5.

In one embodiment, up to five amino acid substitutions may be made to de-immunize the modified IgG antibodies. De-immunization may be performed according to the method of Harding et al. (2010) *mAbs* 2: 256-265, for example.

Framework residues of the VH and/or VL domains, for example, may be substituted to increase the stability of the modified IgG antibodies and/or decrease their tendency to aggregate. Poor stability can affect the ability of the expressed modified IgG antibodies to fold properly when recombinantly expressed, resulting in a fraction of the expressed antibodies being non-functional. Low stability antibodies also may be prone to forming potentially immunogenic aggregates or may have impaired avidity or shelf-life. Framework amino acid substitutions that are expected to increase the stability and/or decrease the tendency to aggregate of a VH and/or VL domain, e.g., in a modified IgG antibody, are disclosed in WO 2007/109254, for example. Substitutions in corresponding residues in the present VH and VL domains are expected similarly to increase stability and/or decrease the tendency of modified IgG antibodies to aggregate.

Substitutions that can be tolerated are expected to include those that would replace an amino acid of SEQ ID No. 1, SEQ ID No. 2, SEQ ID No. 3, or SEQ ID No. 4 with a corresponding amino acid that occurs in another human VH or VL domain germline sequence. A substitution of a framework amino acid with an amino acid occurring in any of these germline sequences may be tolerated. For example, a residue of a VH domain of SEQ ID No. 1 may be substituted with an amino acid appearing in a corresponding position in any VH germline sequence, e.g., the germline sequence from DP-10 ($V_H$ 1-69) or DP-88 ($V_H$ 1-e). Corresponding positions in this case are determined by a sequence alignment between the various germline sequences, using alignment techniques well known in the art, e.g., ClustalW.

Additional substitutions that are expected to be tolerated are those made to an amino acid with most of its side chain exposed to the solvent, as determined by analysis of the three co-crystal structures. The solvent-accessible surface area of a residue may be estimated using techniques well known in the art. Further, it is expected that substitutions to amino acids buried within the variable domains will be better tolerated if the side chain of the amino acid does not create steric hindrance with adjoining residues. For this reason, buried amino acids generally are substituted with amino acids with side chains of similar or smaller size. For example, a substitution of a buried Ile residue with a Leu, Val, Ala, or Gly is expected to be tolerated. Possible steric hindrance created by a substitution can be predicted by analysis of the three co-crystal structures. Further substitutions that are expected to be tolerated are those maintaining existing electrostatic interactions within the variable domains, e.g., dipole-dipole interactions, induced dipole interactions, hydrogen bonds, or ionic bonds.

Additional amino acid substitutions of variable domains include those expected to confer new useful properties to the antibodies or antigen-binding fragments thereof. For example, putative N-glycosylation sites in the VH and/or VL domains can be removed to prevent or reduce the formation of N-glycoforms. The amino-terminal residue can be substituted with a Gln residue to cause pyroglutamylation, which can decrease the number of charge variants. Amino acid substitutions can be used to lower the isoelectric point, which can decrease the rate of elimination of IgG polypeptide antibodies, for example.

Surface residues of variable domains can be substituted with Cys or Lys residues, for example, which then can be covalently modified and coupled to molecules conferring useful characteristics to the antibodies or antigen-binding fragments thereof, e.g., a detectable label, toxin, targeting moiety, or protein. For example, Cys residue can be coupled to a cytotoxic drug to form a drug conjugate. Cys residues also can be coupled to molecules that increase the serum half-life, e.g., polyethylene glycol (PEG) or serum albumin. Such amino acid modifications are reviewed in Beck et al. (2010) *Nature* 10: 345-52, for example.

Detectable labels include radiolabels such as $^{131}I$ or $^{99}Tc$, which may be attached to antibodies or antigen-binding fragments thereof using methods known in the art. Labels also include enzyme labels such as horseradish peroxidase. Labels further include chemical moieties such as biotin which may be detected via binding to a specific cognate detectable moiety, e.g., labeled avidin. Other moieties can be attached that facilitate purification. For example, antibodies or antigen-binding fragments thereof can be His-tagged using well-known methods of recombinant modification and expression.

The VL domains of the modified IgG antibodies are linked to the CL domains by a linker, termed Linker1 herein. The VH domains of the modified IgG antibodies are optionally linked to the CH1 domains by a second linker, termed Linker2 herein. Linkers suitable for making modified IgG antibodies are well known in the art. See, e.g., Bird et al. (1988) *Science,* 242: 423-426; Huston et al. (1988) *Proc. Nat'l Acad. Sci. USA* 85: 5879-5883. This can be accomplished by fusing the encoding nucleic acids in-frame and expressing the fusion protein in a suitable host cell, for example.

Linker1 may contain a peptide connecting the VL and CL in an IgG molecule, or a modified version with increased flexibility. For example, it may have the sequence of Leucine-Glutamic acid-Isoleucine-Lysine-$X_p$-$Y_q$-$Z_r$-Arginine-Threonine-Valine-Alanine, wherein X, Y and Z is independently an amino acid selected from the group consisting of Serine, Glycine, Alanine, Valine, Leucine, Isoleucine, and Threonine, and each of p, q and r is independently an integer from 0 to 5. Each of X, Y and Z is preferably Serine and Glycine, and each of p, q and r is 1. In another aspect, p is 0 and each of q and r is 1. In another aspect, p is 1 and each of q and r is 0.

Linker2 may contain a peptide having the sequence of Threonine-Valine-Serine-$A_d$-$B_e$-$C_f$-Serine-Alanine-Serine-Threonine, A, B and C being independently an amino acid selected from the group consisting of Serine, Glycine, Alanine, Valine, Leucine, Isoleucine, and Threonine, and each of d, e and f being independently an integer from 0 to 5.

In another embodiment, a hinge is optionally inserted between the CH1 domain and Fc region of the modified IgG antibodies. In one aspect, the hinge region is a flexible domain that optionally joins the CH1 portion to the Fc region. The flexibility of the hinge region in IgG molecules may allow the Fab arms to adopt a wide range of angles, permitting binding to epitopes spaced variable distances apart. In another aspect, a suitable hinge region includes, for example, the human IgG1 hinge region having the amino acid sequence PKSCDKTHTCPPCPAPELLGGP (SEQ ID No. 5). This sequence corresponds to a portion of the human IgG1 upper hinge, the middle hinge, and an N-terminal portion of the CH2 domain, as disclosed in FIG. 4B of U.S. Pat. No. 8,048,421, for example.

In another embodiment, suitable Fc regions of the modified IgG antibodies contain two or three constant regions. Fc regions may include those from human IgG1, as set forth in SEQ ID No. 6, or IgG4, as set forth in the CH2 and CH3 domains of SEQ ID No. 17. The Fc region of an antibody mediates its serum half-life and effector functions, such as complement-dependent cytotoxicity (CDC), antibody-dependent cellular cytotoxicity (ADCC) and antibody-dependent cell phagocytosis (ADCP).

Modifications can be made to the hinge and Fc region to improve various properties of the modified IgG antibodies. In one embodiment, one, two, three, four, five or up to ten amino acids of a naturally occurring human Fc region can be modified, in addition to modifications of the hinge region. For example, the Fc region can be modified to increase the serum half-life of the modified IgG antibodies. The half-life of an IgG depends on its pH-dependent binding to the receptor FcRn. FcRn, which is expressed on the surface of endothelial cells, binds the IgG in a pH-dependent manner and protects it from degradation. Mutations located at the interface between the $CH_2$ and $CH_3$ domains, for example, have been shown to increase the binding affinity to FcRn and the half-life of IgG1 in vivo. Such modifications are reviewed in Strohl WR., 2009. Optimization of Fc-mediated effector functions of monoclonal antibodies. Curr Opin Biotechnol. 20(6):685-91; and Vaccaro C. et al., 2005. Engineering the Fc region of immunoglobulin G to modulate in vivo antibody levels. Nat Biotechnol. 23(10):1283-8, for example.

Other modifications to the hinge and/or Fc region can increase or reduce effector functions. The four human IgG isotypes bind the activating Fcγ receptors (FcγRI, FcγRIIa, FcγRIIIa), the inhibitory FcγRIIb receptor, and the first component of complement (C1q) with different affinities, resulting in different effector functions. Binding of IgG to the FcγRs or C1q, for example, depends on residues located in the IgG hinge region and $CH_2$ domain. Single or multiple amino acid substitutions of these residues can affect effector function by modulating the IgG interaction with FcγRs or C1q. Other substitutions are known to affect effector function. These modifications are reviewed in Strohl (2009) "Optimization of Fc-mediated effector functions of monoclonal antibodies," *Curr. Opin. Biotechnol.* 20:685-91, for example.

Representative modifications of the hinge and/or Fc region are summarized in Table 1.

TABLE 1

Representative Hinge and Fc Region Modifications

| Isotype | Species | Substitutions | FcR/C1q Binding | Effector Function | Refs |
|---|---|---|---|---|---|
| IgG1 | Human | T250Q/M428L | Increased binding to FcRn | Increased half-life | 1 |
| IgG1 | Human | 1M252Y/S254T/T256E + H433K/N434F | Increased binding to FcRn | Increased half-life | 2 |
| IgG1 | Human | E233P/L234V/L235A/G236 + A327G/A330S/P331S | Reduced binding to FcγRI | Reduced ADCC and CDC | 3, 4 |
| IgG1 | Human | E333A | Increased binding to FcγRIIIa | Increased ADCC and CDC | 5, 6 |
| IgG1 | Human | S239D/A330L/I332E | Increased binding to FcγRIIIa | Increased ADCC | 7, 8 |
| IgG1 | Human | P257I/Q311 | Increased binding to FcRn | Unchanged half-life | 9 |
| IgG1 | Human | K326W/E333S | Increased binding to C1q | Increased CDC | 10 |
| IgG1 | Human | S239D/I332E/G236A | Increased FcγRIIa/FcγRIIb ratio | Increased macrophage phagocytosis | 11 |
| IgG1 | Human | K322A | Reduced binding to C1q | Reduced CDC | 5 |
| IgG4 | Human | S228P | — | Reduced Fab-arm exchange | 12 |
| IgG2a | Mouse | L235E + E318A/K320A/K322A | Reduced binding to FcγRI and C1q | Reduced ADCC and CDC | 10 |

1. Hinton et al. (2004) *J. Biol. Chem.* 279(8): 6213-16.
2. Vaccaro et al. (2005) *Nature Biotechnol.* 23(10): 1283-88.
3. Armour et al. (1999) *Eur. J. Immunol.* 29(8): 2613-24.
4. Shields et al. (2001) *J. Biol. Chem.* 276(9): 6591-604.
5. Idusogie et al. (2000) *J. Immunol.* 164(8): 4178-84.
6. Idusogie et al. (2001) *J. Immunol.* 166(4): 2571-75.
7. Lazaret al. (2006) Proc. *Nat'l Acad. Sci.* USA 103(11): 4005-10.
8. Ryan et al. (2007) *Mol. Cancer Ther.* 6: 3009-18.
9. Datta-Mannan et al. (2007) *Drug Metab. Dispos.* 35: 86-94.
10. Steurer et al. (1995) *J. Immunol.* 155(3): 1165-74.
11. Richards et al. (2008) *Mol. Cancer Ther.* 7(8) : 2517-27.
12. Labrijn et al. (2009) *Nature Biotechnol.* 27(8): 767-71.

Further, recombinant amino acid modifications can be used to decrease structural homogeneity of the expressed polypeptides. A representative example is Peters et al. (2012) *J Biol. Chem.* 287(29): 24525-33, which discloses Cys to Ser substitutions in the IgG4 hinge region that reduce the disulfide bond heterogeneity and increase Fab domain thermal stability. Similarly, Zhang et al. (2010) *Anal. Chem.* 82: 1090-99 disclose engineering the IgG2 hinge region to limit disulfide bond scrambling and the formation of structural isomers in therapeutic applications. Amino acid modifications to a CH3 domain also can be used to delete carboxy-terminal Lys residues to decrease the number of charge variants. Amino acid modifications also can be used to improve the pharmacological function of recombinant antibodies or antigen-binding fragments thereof. For example, amino acid modifications can be used to increase complement activation, enhance antibody-dependent cellular cytotoxicity (ADCC) by increasing FcγRIIIA binding or decreasing FcγRIIIB binding, and/or increase serum half-life by increasing FcRn binding. Such amino acid modifications are reviewed in Beck et al. (2010) *Nature* 10: 345-52, for example.

Nucleic Acids and Methods of Making Modified IgG Antibodies

A further aspect of the present invention provides nucleic acids encoding modified IgG antibodies. The isolated nucleic acid may be a synthetic DNA, a non-naturally occurring mRNA, or a cDNA, for example. Examples include the nucleic acids encoding the VH and VL domains set forth in SEQ ID NOS: 3, 5, 7, and 9 of U.S. Pat. No. 6,492,497. A recombinant host cell may comprise one or more constructs above. Methods of preparing modified IgG antibodies comprise expressing the encoding nucleic acid in a host cell under conditions to produce the modified IgG antibodies, and recovering the antibodies. The process of recovering the antibodies may comprise isolation and/or purification of the antibodies. The method of production may comprise formulating the antibodies into a composition including at least one additional component, such as a pharmaceutically acceptable excipient.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the Kingdoms of life. Preferred enkaryotic cells include protist, fungal, plant and animal cells. Most preferably host cells include but are not limited to the prokaryotic cell line *E.*

*Coli*; mammalian cell lines CHO, HEK 293 and COS; the insect cell line Sf9; and the fungal cell *Saccharomyces cerevisiae.*

Suitable vectors comprising a nucleic acid encoding modified IgG antibodies can be chosen or constructed, containing appropriate regulatory sequences, including promoter sequences, terminator sequences, polyadenylation sequences, enhancer sequences, marker genes and other sequences as appropriate. Vectors may be plasmids, phage, phagemids, adenoviral, AAV, lentiviral, for example. Techniques and protocols for manipulation of nucleic acid, for example in preparation of nucleic acid constructs, mutagenesis, sequencing, introduction of DNA into cells, and gene expression, are well known in the art.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adena-associated viruses), which serve equivalent functions.

Introducing such nucleic acids into a host cell can be accomplished using techniques well known in the art. For eukaryotic cells, suitable techniques may include calcium phosphate transfection, DEAE-Dextran, electroporation, liposome-mediated transfection, and transduction using retroviruses or other viruses, for example. For bacterial cells, suitable techniques may include calcium chloride transformation, electroporation, and transfection using bacteriophage. The introduction may be followed by causing or allowing expression from the nucleic acid, e.g. by culturing host cells under conditions for expression of the gene. In one embodiment, the nucleic acid of the invention is integrated into the genome, e.g., chromosome, of the host cell. Integration may be promoted by inclusion of sequences which promote recombination with the genome, in accordance with standard techniques.

Systems for cloning and expression of a polypeptide in a variety of different host cells are well known. Suitable host cells include bacteria, mammalian cells, plant cells, insect cells, fungi, yeast and transgenic plants and animals. Mammalian cell lines available in the art for expression of a heterologous polypeptide include Chinese hamster ovary (CHO) cells, HeLa cells, baby hamster kidney cells, mouse melanoma cells, rat myeloma cells, human embryonic kidney cells, e.g., HEK293 cells, human embryonic retina cells, and many others. The expression of antibodies and antibody fragments in prokaryotic cells, such as *E. coli*, is well established in the art. For a review, see for example, Plückthun *Bio/Technology* 9: 545-551 (1991). Expression in cultured eukaryotic cells is also available to those skilled in the art, as reviewed in Andersen et al. (2002) *Curr. Opin. Biotechnol.* 13: 117-23, for example.

In another embodiment, the disclosed modified IgG antibodies may be glycosylated, either naturally or the choice of expression host, e.g., CHO, HEK293, or NSO (ECACC 85110503) cells, or they may be unglycosylated, for example if produced by expression in a prokaryotic cell. Glycosylation may also be intentionally altered, for example by inhibiting fucosylation, in order to increase ADCC activity of the resulting modified IgG antibodies.

Methods of Using Antibodies or Antigen-Binding Fragments Thereof

The modified IgG antibodies may be used in a method of treatment or diagnosis of the human or animal body, such as a method of treatment (which may include prophylactic treatment) of a disease or disorder in a human patient, which comprises administering an effective amount to treat the patient. Treatable conditions include any in which TGFβ1 plays a role, e.g., a fibrotic disease, cancer, an immune-mediated disease, and wound healing, e.g., diffuse systemic sclerosis, bone remodeling disease, kidney disease and/or a combination thereof.

Antibodies specific for human TGFβ1 have been shown to be effective in animal models for the treatment of TGFβ1 glomerulonephritis (Border et al. (1990) *Nature* 346: 371-374), neural scarring (Logan et al. (1994) *Eur. J. Neurosci.* 6: 355-363), dermal scarring (Shah et al. (1992) *Lancet* 339: 213-214; Shah et al. (1994) *J. Cell Science* 107: 1137-1157; Shah et al. (1995) *J. Cell Science* 108: 985-1002), and pulmonary fibrosis (Giri et al. (1993) *Thorax* 48: 959-966). Further, antibodies to TGFβ1, 2, and 3 have been shown to be effective in models of lung fibrosis, radiation induced fibrosis (U.S. Pat. No. 5,616,561), myelofibrosis, burns, Dupuytren's contracture, gastric ulcers, and rheumatoid arthritis (Wahl et al. (1993) *Exp. Medicine* 177: 225-230).

The modified IgG antibodies are useful to treat a disease and condition resulting directly or indirectly from TGFβ1 activity. The modified IgG antibodies may selectively inhibit the activity of a human TGFβ1 isoform in vitro or in vivo. Activities of TGFβ1 isoforms include, but are not limited to, TGFβ-mediated signaling, extracellular matrix (ECM) deposition, inhibiting epithelial and endothelial cell proliferation, promoting smooth muscle proliferation, inducing Type III collagen expression, inducing TGF-β, fibronectin, VEGF, and IL-11 expression, binding Latency Associated Peptide, tumor-induced immunosuppression, promotion of angiogenesis, activating myofibroblasts, promotion of metastasis, and inhibition of NK cell activity. For example, the modified IgG antibodies are useful to treat focal segmental glomerulosclerosis (FSGS), hepatic fibrosis (HF), acute myocardial infarction (AMI), idiopathic pulmonary fibrosis (IPF), scleroderma (SSc), and Marfan Syndrome.

The modified IgG antibodies are useful to treat diseases and conditions including, but not limited to, fibrotic diseases (such as glomerulonephritis, neural scarring, dermal scarring, pulmonary fibrosis, lung fibrosis, radiation induced fibrosis, hepatic fibrosis, myelofibrosis), burns, immune mediated diseases, inflammatory diseases (including rheumatoid arthritis), transplant rejection, cancer, Dupuytren's contracture, and gastric ulcers. The modified IgG antibodies are also useful for treating, preventing and reducing the risk of occurrence of renal insufficiencies including but not limited to: diabetic (type I and type II) nephropathy, radiation-induced nephropathy, obstructive nephropathy, diffuse systemic sclerosis, pulmonary fibrosis, allograft rejection, hereditary renal disease (e.g., polycystic kidney disease, medullary sponge kidney, horseshoe kidney), glomerulonephritis, nephrosclerosis, nephrocalcinosis, systemic lupus erythematosus, Sjogren's syndrome, Berger's disease, systemic or glomerular hypertension, tubulointerstitial nephropathy, renal tubular acidosis, renal tuberculosis, and renal infarction. In particular, the modified IgG antibodies are useful when combined with antagonists of the renin-angiotensin-aldosterone system including, but not limited to: renin inhibitors, angiotensin-converting enzyme (ACE) inhibitors, Ang II receptor antagonists (also known as "Ang II receptor blockers"), and aldosterone antagonists. By way of example, methods for using modified IgG antibodies in combination with such antagonists are set forth in WO 2004/098637.

The modified IgG antibodies also are useful to treat diseases and conditions associated with the deposition of ECM, including, systemic sclerosis, postoperative adhesions, keloid and hypertrophic scarring, proliferative vitreoretinopathy, glaucoma drainage surgery, corneal injury, cataract, Peyronie's disease, adult respiratory distress syndrome, cirrhosis of the liver, post myocardial infarction scarring, post angioplasty restenosis, scarring after subarachnoid hemorrhage, multiple sclerosis, fibrosis after laminectomy, fibrosis after tendon and other repairs, scarring due to tattoo removal, biliary cirrhosis (including sclerosing cholangitis), pericarditis, pleurisy, tracheostomy, penetrating central nervous system injury, eosinophilic myalgic syndrome, vascular restenosis, veno-occlusive disease, pancreatitis and psoriatic arthropathy.

The modified IgG antibodies further are useful to promote re-epithelialization in diseases and conditions such as venous ulcers, ischaemic ulcers (pressure sores), diabetic ulcers, graft sites, graft donor sites, abrasions and burns, diseases of the bronchial epithelium, such as asthma, ARDS, diseases of the intestinal epithelium, such as mucositis associated with cytotoxic treatment, esophageal ulcers (reflux disease), stomach ulcers, small intestinal and large intestinal lesions (inflammatory bowel disease).

The modified IgG antibodies also may be used to promote endothelial cell proliferation, for example, in stabilizing atherosclerotic plaques, promoting healing of vascular anastomoses, or to inhibit smooth muscle cell proliferation, such as in arterial disease, restenosis and asthma.

The modified IgG antibodies are useful to enhance the immune response to macrophage-mediated infections. They are also useful to reduce immunosuppression caused, for example, by tumors, AIDS, or granulomatous diseases. The modified IgG antibodies are useful to treat hyperproliferative diseases, such as cancers including, but not limited to, breast, prostate, ovarian, stomach, renal, pancreatic, colorectal, skin, lung, cervical and bladder cancers, glioma, mesothelioma, as well as various leukemias and sarcomas, such as Kaposi's sarcoma, and are useful to treat or prevent recurrences or metastases of such tumors. Modified IgG antibodies also are useful to inhibit cyclosporin-mediated metastases.

In the context of cancer therapy, "treatment" includes any medical intervention resulting in the slowing of tumor growth or reduction in tumor metastases, as well as partial remission of the cancer in order to prolong life expectancy of a patient.

Methods of treatment comprise administering a modified IgG antibody or pharmaceutical compositions comprising the modified IgG antibody. The modified IgG antibodies may be used in the manufacture of a medicament for administration. For example, a method of making a medicament or pharmaceutical composition comprises formulating a modified IgG antibody with a pharmaceutically acceptable excipient. A composition may be administered alone or in combination with other treatments, either simultaneously or sequentially dependent upon the condition to be treated.

Administration is preferably in a "therapeutically effective amount" sufficient to show benefit to a patient. Such benefit may be at least amelioration of at least one symptom of a particular disease or condition. The actual amount administered, and rate and time-course of administration, will depend on the nature and severity of the disease or condition being treated. Prescription of treatment, e.g., decisions on dosage etc., may be determined based on preclinical and clinical studies the design of which is well within the level of skill in the art.

The precise dose will depend upon a number of factors, including whether the modified IgG antibody is for diagnosis or for treatment, the size and location of the area to be treated, and the nature of any detectable label or other molecule attached to the modified IgG antibody. A typical dose of a modified IgG antibody, for example, can be in the range 100 μg to 1 gram for systemic applications, and 1 μg to 1 mg for topical applications. The dose for a single treatment of an adult patient may be adjusted proportionally for children and infants. Treatments may be repeated at daily, twice-weekly, weekly, monthly or other intervals, at the discretion of the physician. Treatment may be periodic, and the period between administrations is about two weeks or more, preferably about three weeks or more, more preferably about four weeks or more, or about once a month.

In one embodiment, dose levels of about 0.1, 0.3, 1, 3, 10, 15 mg, or 20 mg of the disclosed antibodies per kg body weight of the patient may be useful and safe in humans. For example, 0.5-5 mg/kg in rat and mouse has been an effective dose in an acute setting. Therefore, for long-term dosing, 0.3-10 mg/kg may be administered to humans, based on an expected half-life of 21 days. Doses may be sufficient for efficacy, while low enough to facilitate optimal administration. For example, a dose of less than 50 mg facilitates subcutaneous administration. Intravenous administration may be used as the route of delivery for severe diseases, where high doses and the long dosing intervals may be required. Subcutaneous injection can increase the potential immune response to a product. Local administration for localized disease can reduce the amount of administered product and increase the concentration at the site of action, which can improve safety.

Modified IgG antibodies may be administered by injection, for example, subcutaneously, intravenously, intracavity (e.g., after tumor resection), intralesionally, intraperitoneally, or intramuscularly. Modified IgG antibodies also may be delivered by inhalation or topically (e.g., intraocular, intranasal, rectal, into wounds, on skin), or orally.

A modified IgG antibody will usually be administered in the form of a pharmaceutical composition, which may comprise at least one component in addition to the modified IgG antibody. Thus pharmaceutical compositions may comprise a pharmaceutically acceptable excipient, carrier, buffer, stabilizer or other materials well known to those skilled in the art. Such materials should be non-toxic and should not interfere with the efficacy of the active ingredient. Such materials could include, for example, any and all solvents, dispersion media, coatings, antibacterial and antifungal agents, isotonic, and absorption delaying agents. Some examples of pharmaceutically acceptable carriers are water, saline, phosphate buffered saline, dextrose, glycerol, ethanol, and the like, as well as combinations thereof. In many cases, it will be preferable to include isotonic agents, for example, sugars, polyalcohols, such as mannitol, sorbitol, or sodium chloride in the composition. Additional examples of pharmaceutically acceptable substances are wetting agents or auxiliary substances, such as emulsifying agents, preservatives, or buffers, which increase the shelf life or effectiveness.

The precise nature of the carrier or other material will depend on the route of administration. For intravenous injection, or injection at the site of affliction, the active ingredient will be in the form of a parenterally acceptable aqueous solution which is pyrogen-free and has suitable pK, isotonicity, and stability. Those of relevant skill in the art are well able to prepare suitable solutions using, for example, isotonic vehicles such as sodium chloride injection, Ringer's injection, and lactated Ringer's injection. Preservatives, stabilizers, buffers, antioxidants, and/or other additives may be included.

A modified IgG antibody may be formulated in liquid, semi-solid, or solid forms, such as liquid solutions (e.g., injectable and infusible solutions), dispersions or suspensions, powders, liposomes, and suppositories. The preferred form depends on the intended mode of administration, the therapeutic application, the physicochemical properties of the molecule, and the route of delivery. Formulations may include excipients, or a combination of excipients, for example: sugars, amino acids and surfactants. Liquid formulations may include a wide range of modified IgG antibody concentrations and pH. Solid formulations may be produced by lyophilization, spray drying, or drying by supercritical fluid technology, for example.

Therapeutic compositions can be formulated as a solution, microemulsion, dispersion, liposome, or other ordered structure suitable to high drug concentration. Sterile injectable solutions can be prepared by incorporating the modified IgG antibody in an appropriate solvent with one or a combination of ingredients enumerated above, followed by filtered sterilization. Generally, dispersions are prepared by incorporating the active compound into a sterile vehicle that contains a basic dispersion medium and other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by using a coating such as lecithin, by maintaining the particle size of a dispersion, or by using surfactants. Prolonged absorption of injectable compositions can be brought about by including in the composition an agent that delays absorption, for example, monostearate salts and gelatin.

In certain embodiments, the active compound may be prepared with a carrier that will protect the modified IgG antibody against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

A method of using a modified IgG antibody may comprise causing or allowing binding to TGFβ. Such binding may take place in vivo, e.g., following administration of a modified IgG antibody to a patient, or it may take place in vitro, e.g., in ELISA, Western blotting, immunocytochemistry, immunoprecipitation, affinity chromatography, or cell based assays, or in ex vivo based therapeutic methods, e.g., methods in which cells or bodily fluids are contacted ex vivo with a modified IgG antibody and then administered to a patient.

A kit comprising a modified IgG antibody is provided. The modified IgG antibody may be labeled to allow its reactivity in a sample to be determined. Kits may be employed in diagnostic analysis, for example. A kit may contain instructions for use of the components. Ancillary materials to assist in or to enable performing such a method may be included within the kit.

The reactivity of a modified IgG antibody in a sample may be determined by any appropriate means, e.g., radioimmunoassay (RIA). Radioactively labeled antigen may be mixed with unlabeled antigen (the test sample) and allowed to bind to the modified IgG antibody. Bound antigen is physically separated from unbound antigen and the amount of radioactive antigen bound to the modified IgG antibody is determined. A competitive binding assay also may be used with non-radioactive antigen, using an antigen or an analogue linked to a reporter molecule. The reporter molecule may be a fluorochrome, phosphor, or dye. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are colored, magnetic or paramagnetic, and biologically or chemically active agents that can directly or indirectly cause detectable signals to be visually observed, electronically detected or otherwise recorded. These molecules may be enzymes that catalyze reactions that develop or change colors or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed. The signals generated by antibody-reporter conjugates may be used to derive quantifiable absolute or relative data of the relevant antibody binding in samples.

The present invention also provides the use of a modified IgG antibody for measuring antigen levels in a competition assay. The modified IgG antibody can be linked to a reporter molecule so that a physical or optical change occurs on binding, for example. The reporter molecule may directly or indirectly generate detectable, and preferably measurable, signals. The reporter molecules may be linked directly or indirectly, covalently, e.g., via a peptide bond or non-covalently. The modified IgG antibody and a protein reporter may be linked by a peptide bond and recombinantly expressed as a fusion protein.

Further aspects and embodiments of the present invention will be apparent to those skilled in the art in the light of the present disclosure, including the following experimental exemplification.

EXAMPLES

Example 1: Modified IgG4 Antibody with Additional Amino Acids in the Light Chain Elbow Region CAT192 is a TGFβ1-specific antibody, but most of its binding affinity was lost when it was converted from a scFv into a full-length IgG4 (FIG. 1). Antibody subtype and Fc formats alone do not explain this phenomenon because both IgG1 and IgG4 Fab displayed very low affinity to TGFβ1. The tight binding of scFv to TGFβ1 may be due to the high flexibility resulting from the long $(GGGGS)_3$ (SEQ ID NO:64) linker connecting the heavy and light chain Fv domains. This high flexibility may have been lost during conversion of the scFv to Fab or IgG versions. The low affinity of CAT192 was characterized by a very slow on-rate but also a very slow off-rate. The slow on-rate and off-rate suggested that the binding between CAT192 and TGFβ1 may require a potential conformational change which was limited by unfavorable amino acids in CAT192(IgG4). Described here are experiments designed to increase flexibility/affinity of the Fab or IgG versions of the scFv by adding additional amino acids in the light chain elbow region, which links the antibody Fv domain to the CH1 domain. More specifically, mutants were designed to add one glycine (G), two glycines (GG), two glycines and one serine (GGS), three glycines and one serine (GGGS; SEQ ID NO: 62), and four glycines and one serine (GGGGS; SEQ ID NO: 63) sequences into the wild-type light chain elbow region as shown below in Table 2, with the added amino acids underlined.

TABLE 2

Modified-IgG4 Light Chain Elbow Region Insertion Mutants

| Name | Position | Amino acid sequence |
|---|---|---|
| WT | Light chain elbow region | LEIKRTVA (SEQ ID No. 21) |
| LC + G | Light chain elbow region | LEIK<u>G</u>RTVA (SEQ ID No. 22) |
| LC + GG | Light chain elbow region | LEIK<u>GG</u>RTVA (SEQ ID No. 23) |
| LC + GGS | Light chain elbow region | LEIK<u>GGS</u>RTVA (SEQ ID No. 24) |
| LC + GGGS | Light chain elbow region | LEIK<u>GGGS</u>RTVA (SEQ ID No. 25) |
| LC + GGGGS | Light chain elbow region | LEIK<u>GGGGS</u>RTVA (SEQ ID No. 26) |
| A25S | Light chain Fv | Ala25→Ser25 |

The light chain amino acid #25 is an Ala in scFv, but was changed to Ser when converted to IgG4. Therefore, an additional A25S mutant was included as a control to test whether changing the Ala to Ser affects the affinity of the scFv to TGFβ1. The wild-type CAT192 and the mutant DNA and amino acid sequences are listed below.

SEQ ID No. 38: Amino acid sequence of CAT192 IgG1 Wild-Type LC with the elbow region underlined:
EIVLTQSPSSLSASVGDRVTITCRASQGIGDDLGWYQQKPGKAPILLIYGTSTL QSGVPSRFSGSGSGTDFTLTINSLQPEDFATYYCLQDSNYPLTFGGGTR<u>LEIKR</u>

<u>TVA</u>APSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGE

C

SEQ ID No. 27: Coding sequence of CAT192 (IgG1) Light Chain
atgggctggtcctgcatcatcctgtttctggtggccacagccaccggcgtgcacagcGAGATCGTGCTGACA

CAGAGCCCCAGCAGCCTGTCTGCCAGCGTGGGCGACAGAGTGACCATCAC

CTGTAGAGCCAGCCAGGGCATCGGCGACGACCTGGGATGGTATCAGCAGA

AGCCTGGCAAGGCCCCCATCCTGCTGATCTACGGCACCAGCACACTGCAG

AGCGGCGTGCCCTCCAGATTTTCTGGCAGCGGCTCCGGCACCGACTTCACC

CTGACCATCAACAGCCTGCAGCCCGAGGACTTCGCCACCTACTACTGTCTG

CAAGACAGCAACTACCCCCTGACCTTCGGCGGAGGCACCCGGCTGGAAAT

CAAGCGTACGGTGGCCGCTCCTTCCGTGTTCATCTTCCCTCCCTCCGACGA

GCAGCTGAAGTCCGGCACCGCCTCCGTGGTGTGTCTGCTGAACAACTTCTA

CCCTCGGGAGGCCAAGGTGCAGTGGAAGGTGGACAACGCCCTGCAGTCCG

GCAACTCCCAGGAGTCCGTCACCGAGCAGGACTCCAAGGACAGCACCTAC

-continued

```
TCCCTGTCCTCCACCCTGACCCTGTCCAAGGCCGACTACGAGAAGCACAA

GGTGTACGCCTGTGAGGTGACCCACCAGGGCCTGTCCAGCCCTGTGACCA

AGTCCTTCAACCGGGGCGAGTGCTGA

CAT192LC + G (LEIKGRTVA)
Forward 5'-ggctggaaatcaagggccgtacggtggccgc-3' (SEQ ID No. 28)

Complement 5'-gcggccaccgtacggcccttgatttccagcc-3' (SEQ ID No. 29)

CAT192LC + GG. (LEIKGGRTVA)
Forward 5'-ggctggaaatcaagggcggccgtacggtggccgc-3' (SEQ ID No. 30)

Complement 5'-gcggccaccgtacggccgcccttgatttccagcc-3' (SEQ ID No. 31)

CAT192LC + GGS. (LEIKGGSRTVA)
Forward 5'-ggctggaaatcaagggcggcagccgtacggtggccgc-3' (SEQ ID No. 32)

Complement 5'-gcggccaccgtacggctgccgcccttgatttccagcc-3' (SEQ ID No. 33)

CAT192LC + GGGS. (LEIKGGGSRTVA)
Forward 5'-ggctggaaatcaagggcggcggcagccgtacggtggccgc-3' (SEQ ID No. 34)

Complement 5'-gcggccaccgtacggctgccgccgcccttgatttccagcc-3' (SEQ ID No. 35)

CAT192LC + GGGGS. (LEIKGGGGSRTVA)
Forward 5'-ggctggaaatcaagggcggcggcggcagccgtacggtggccgc-3' (SEQ ID No. 36)

Complement 5'-gcggccaccgtacggctgccgccgccgcccttgatttccagcc-3' (SEQ ID No. 37)
```

The five CAT192 LC mutants, along with the A25S mutant and WT LC were co-expressed with His-tagged CAT192 HC Fab using the Expi293F transfection system (Life Technologies) in a 24-well plate format (4×1 mL). Conditioned media (CM) was harvested 4 days post-transfection and the Octet QK384 instrument was used to calculate expression level and TGFβ1 binding in a single assay. Purified CAT192 Fab-His was used as a standard curve (diluted 2-fold from 100 to 3.125 μg/mL). The CAT192 Fab CM was diluted 1:10 in diluent and GC1008 Fab CM was included as positive control. Binding to anti-Fab-CH1 biosensors was measured for 2 min at 1000 rpm and 30° C. plate temperature for quantitation and capture. The sensors were then moved into wells containing 200 nM of TGFβ1 for binding assessment.

The TGFβ1 binding result showed that each additional amino acid insertion increased the binding affinity of the CAT192 Fab as compared to the WT counterpart. Addition of at least two glycines increased the binding affinity to a level comparable to that of the GC1008 Fab antibody. The A25S mutant showed weak TGFβ1 binding affinity, similar to the affinity of the WT and the purified recombinant CAT192 Fab. This result was qualitative because the amount of Fab captured to the sensors was not normalized for concentration or buffer subtracted.

The CAT192 LC Fab variants were then purified using PureSpeed IMAC tips from Rainin in order to accurately assess the affinity to TGFβ1 and confirm isoform-specificity using surface plasmon resonance. The conditioned media for each sample was split into four wells (~800 μL each) and ~200 μL equilibration buffer was added to each in order to use two 1 mL purification tips (20 μL resin) for each sample. The samples were buffer exchanged using Amicon Ultra filters into Gibco PBS pH 7.2 after the elution step to remove the imidazole. The concentrations were measured by A280 and 3.5 μg was loaded onto a non-reducing 4-20% Tris-Glycine SDS-PAGE gel and Coomassie stained to check the purity. The overall yield ranged from 12-42% of the starting material in CM.

Figure 6:
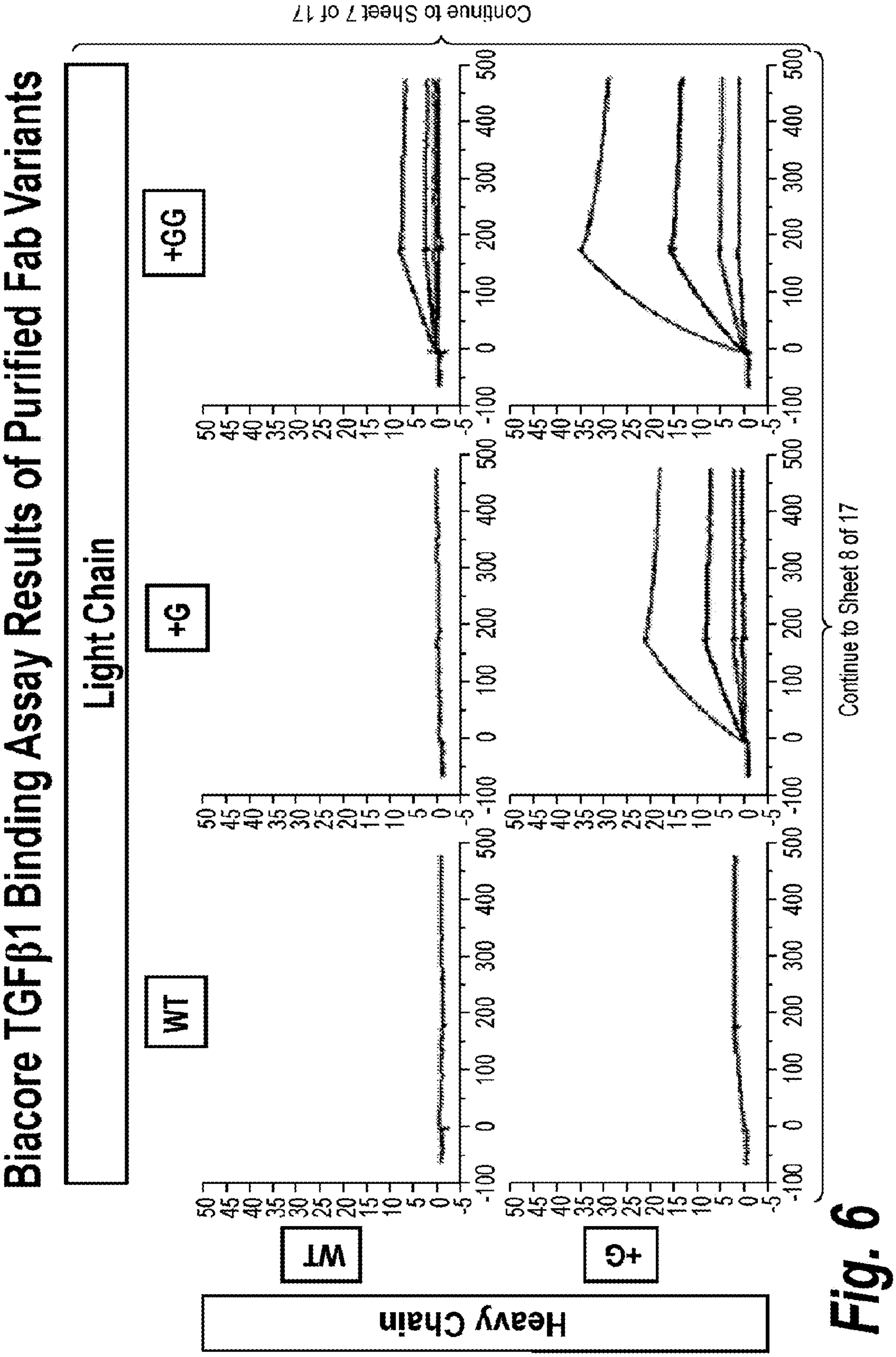
FIG. 6 depicts a Biacore TGFβ1 binding assay which shows high affinity binding is regained when additional amino acids are inserted into the elbow region of both the heavy and light chain of CAT192 Fab.
Figure 6:
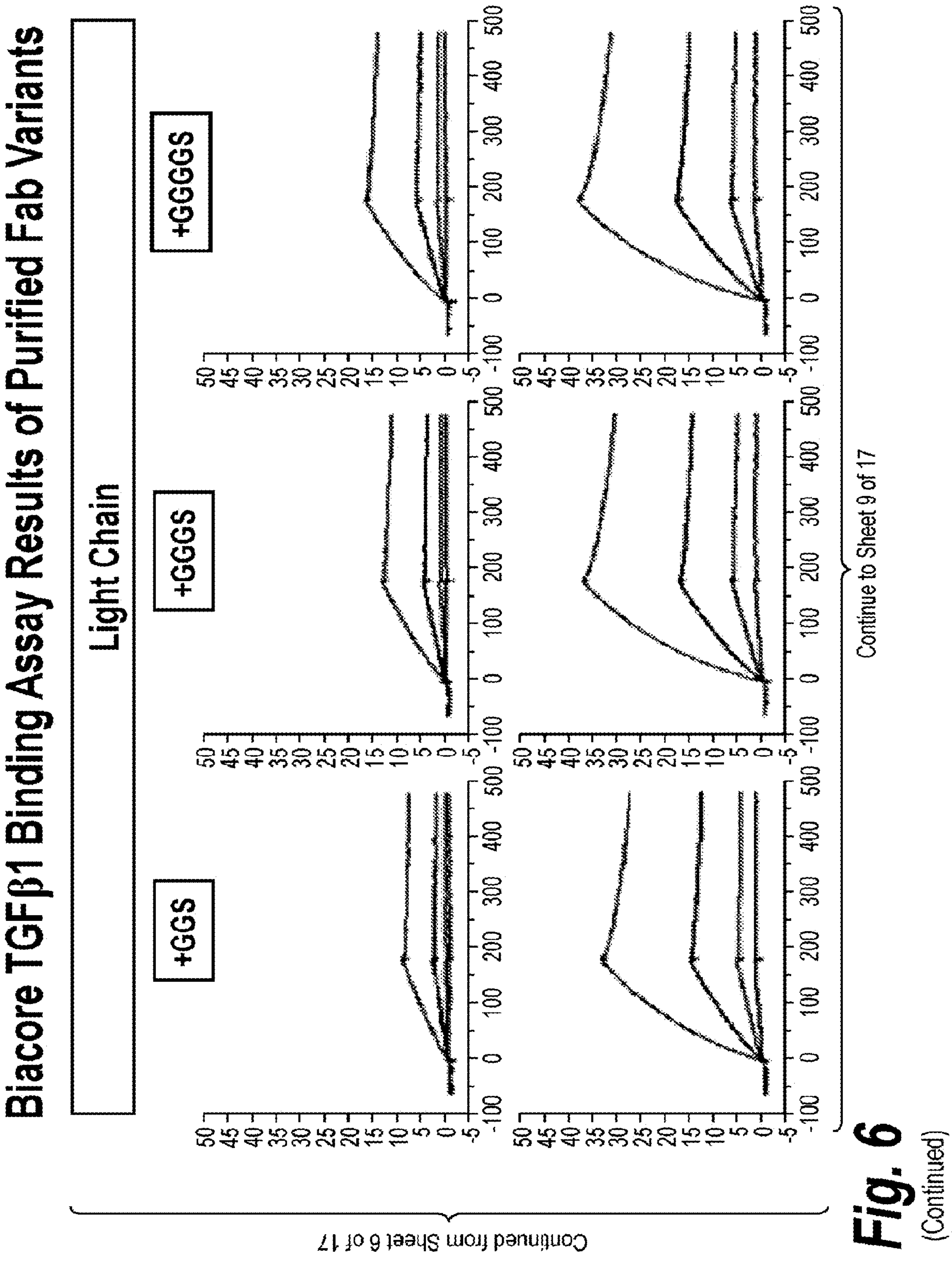
Figure 6:
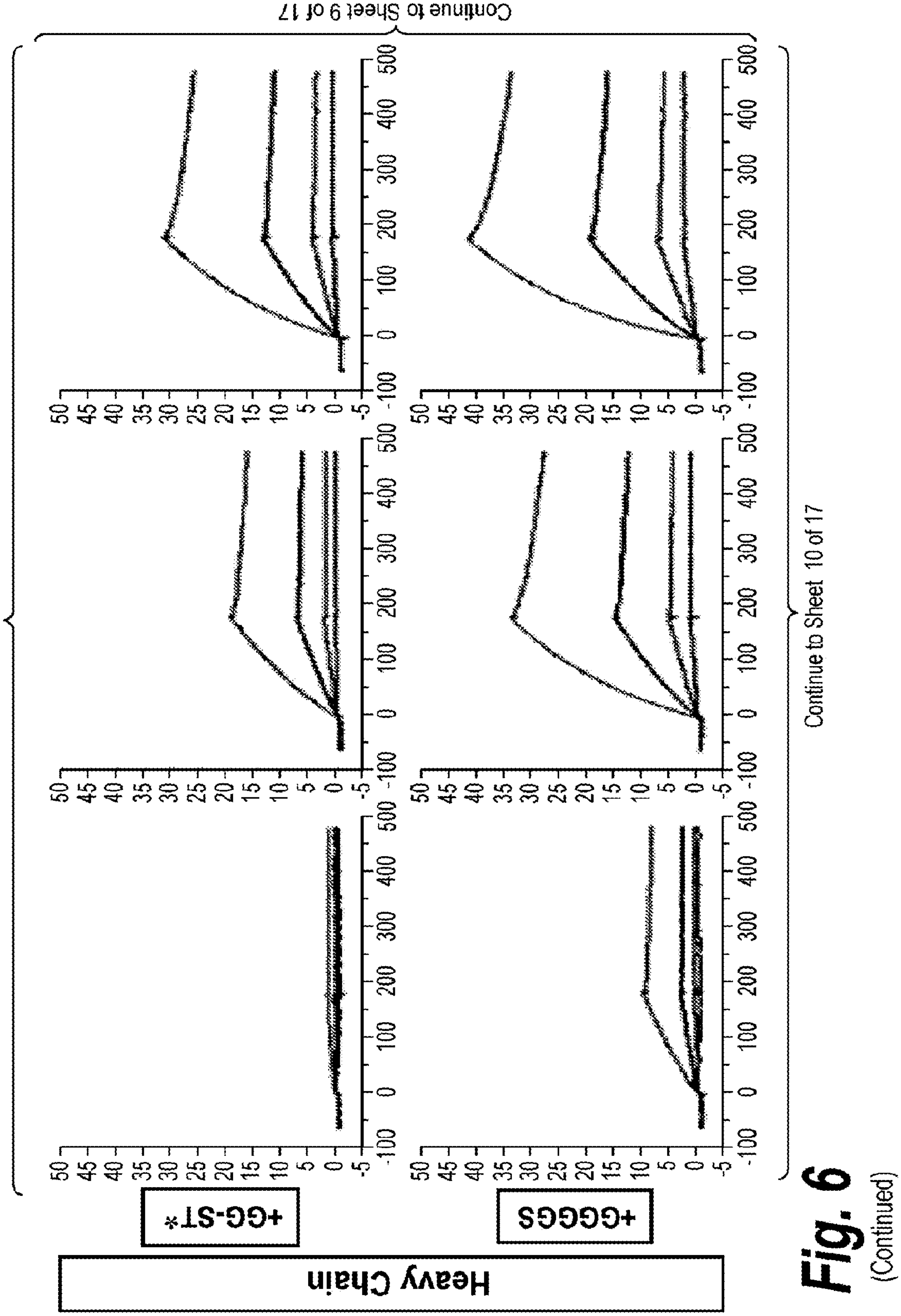
Figure 6:
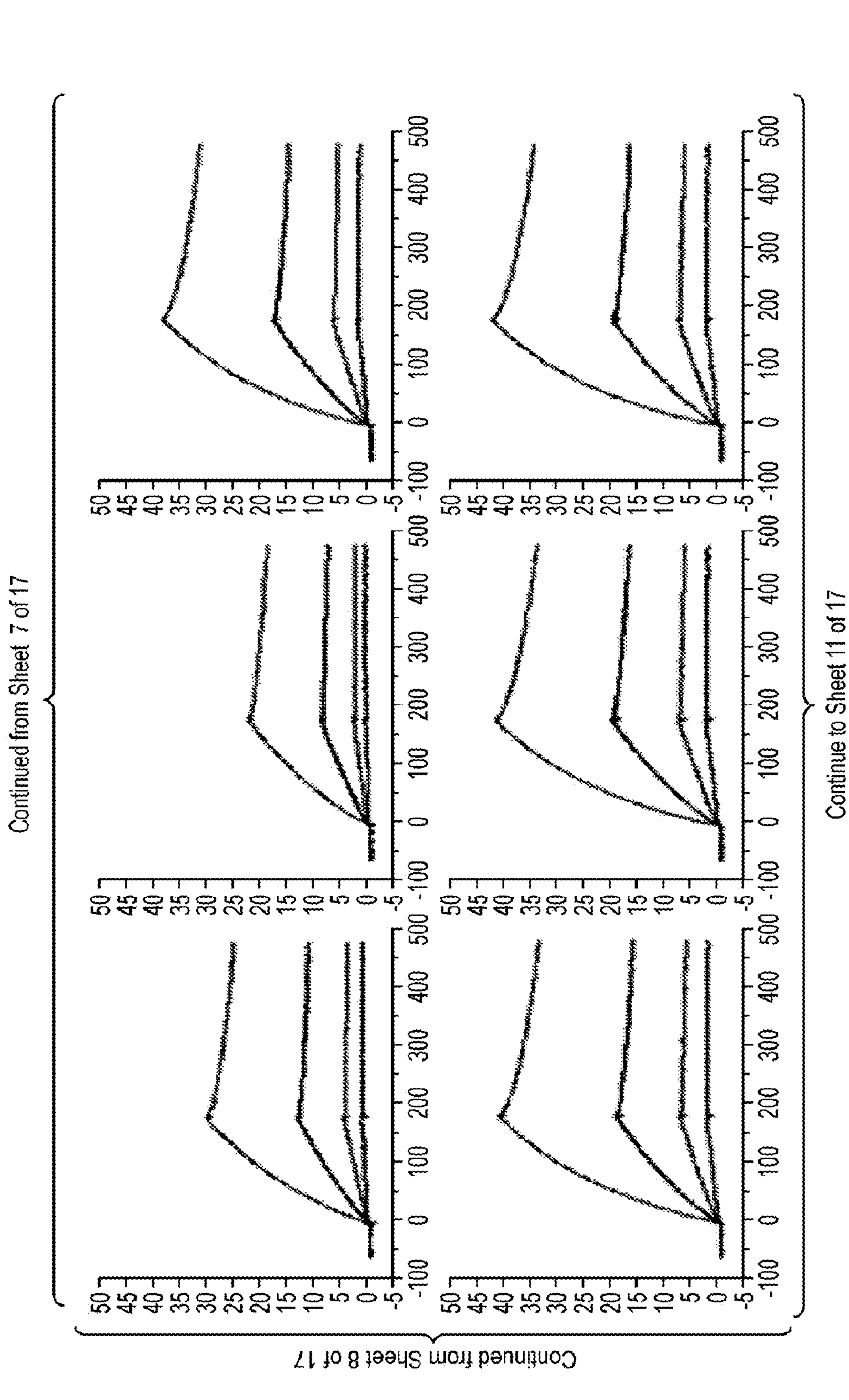
Figure 6:
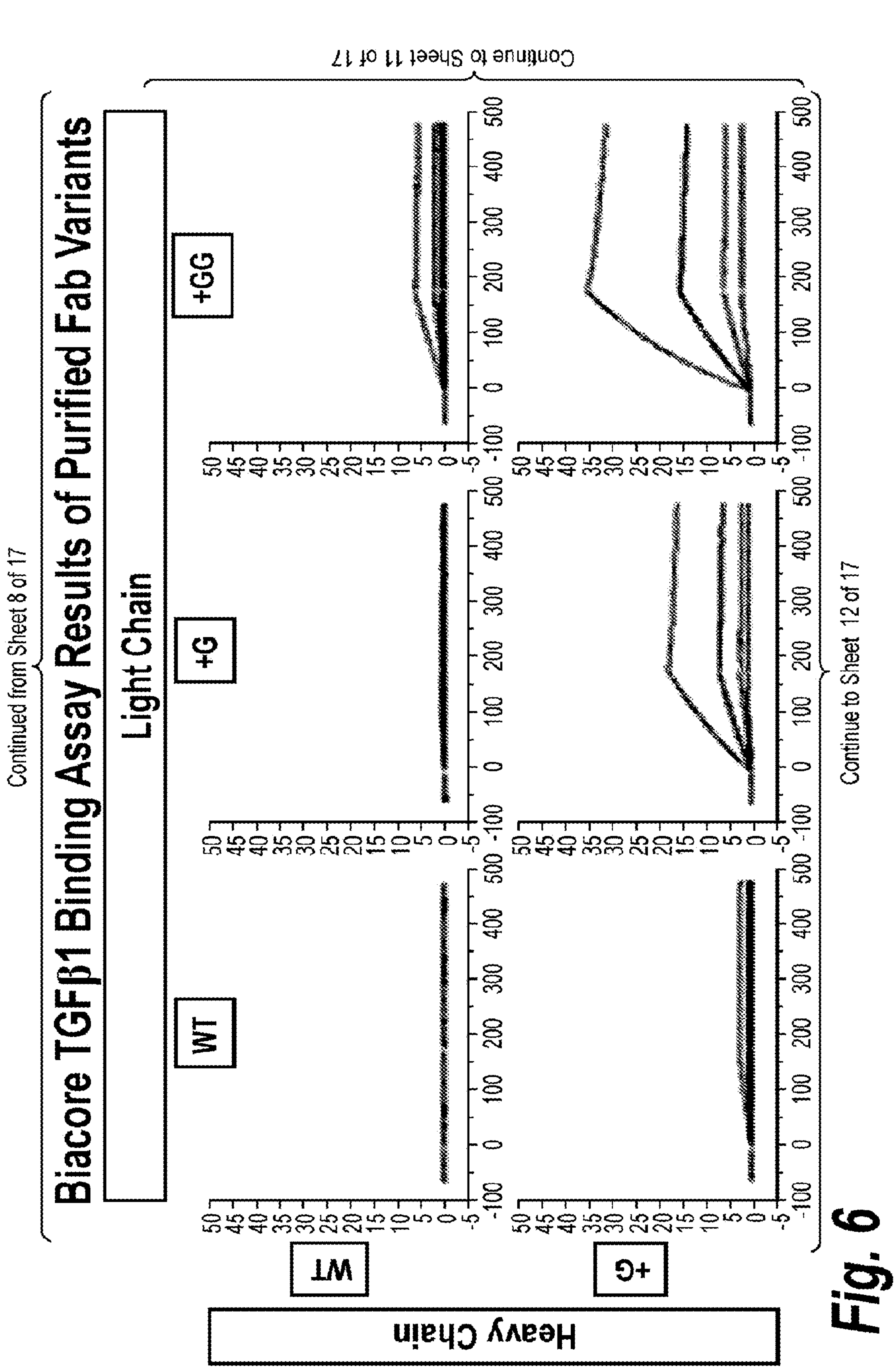
Figure 6:
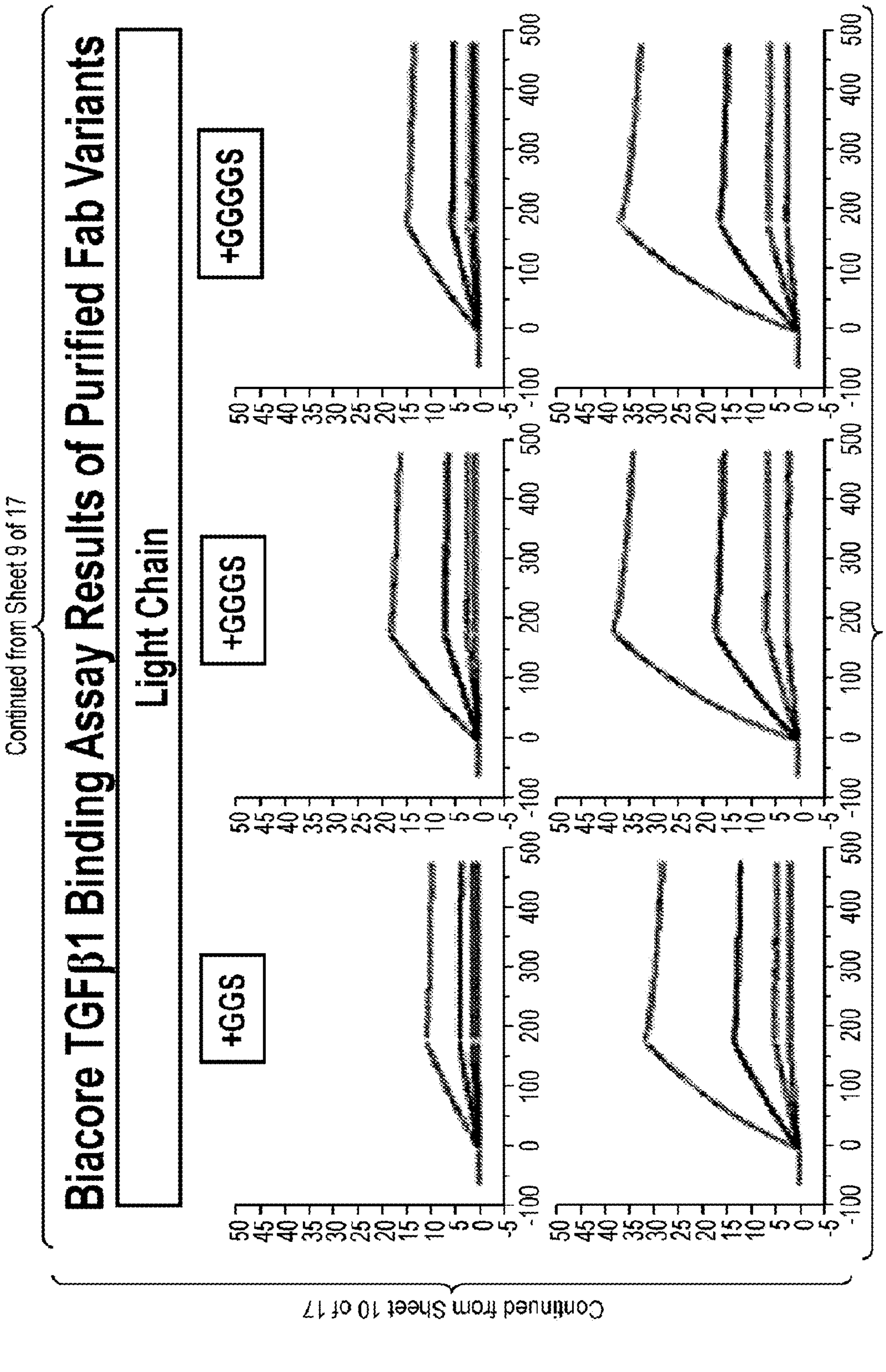
Figure 6:
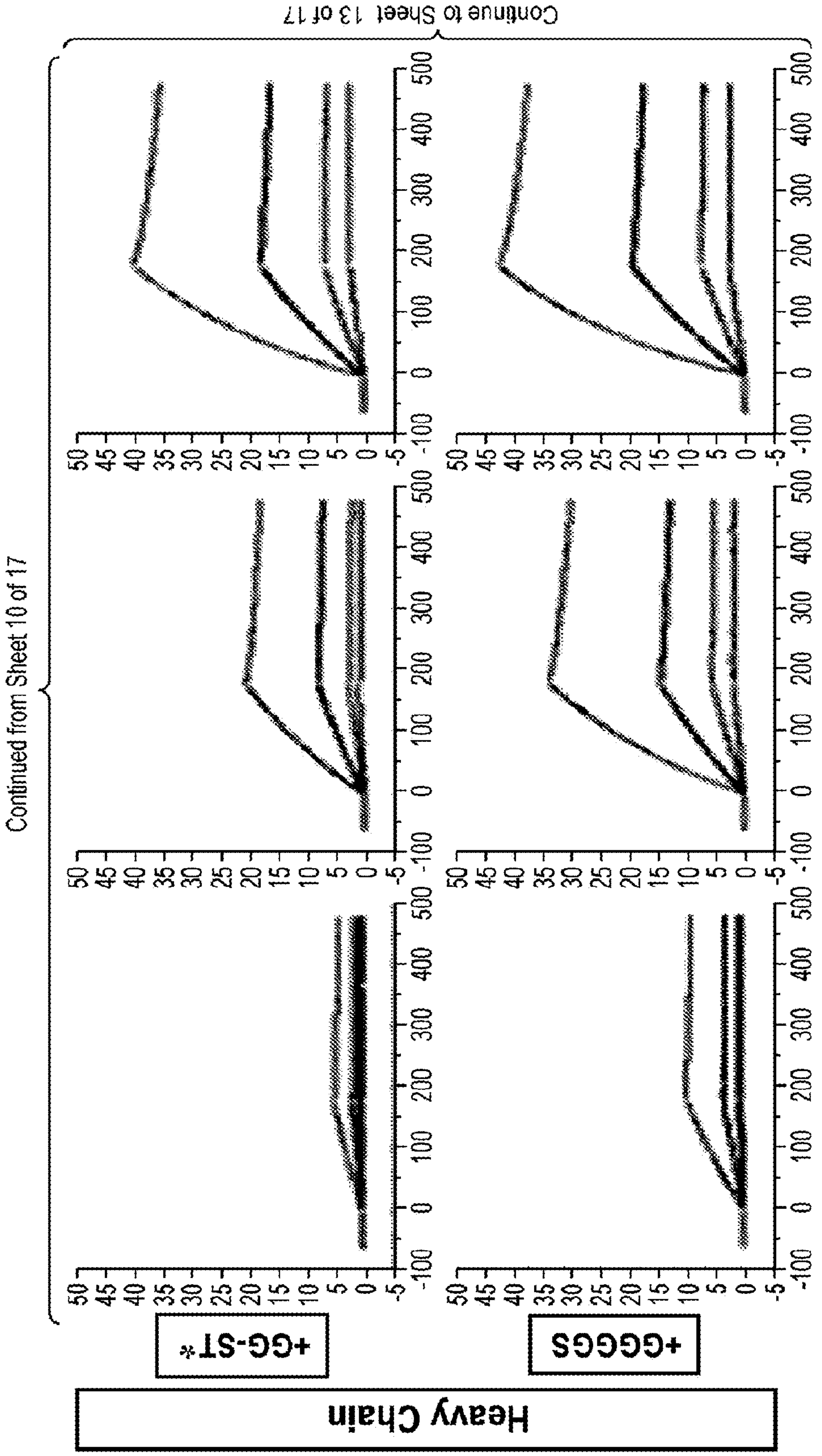
Figure 6:
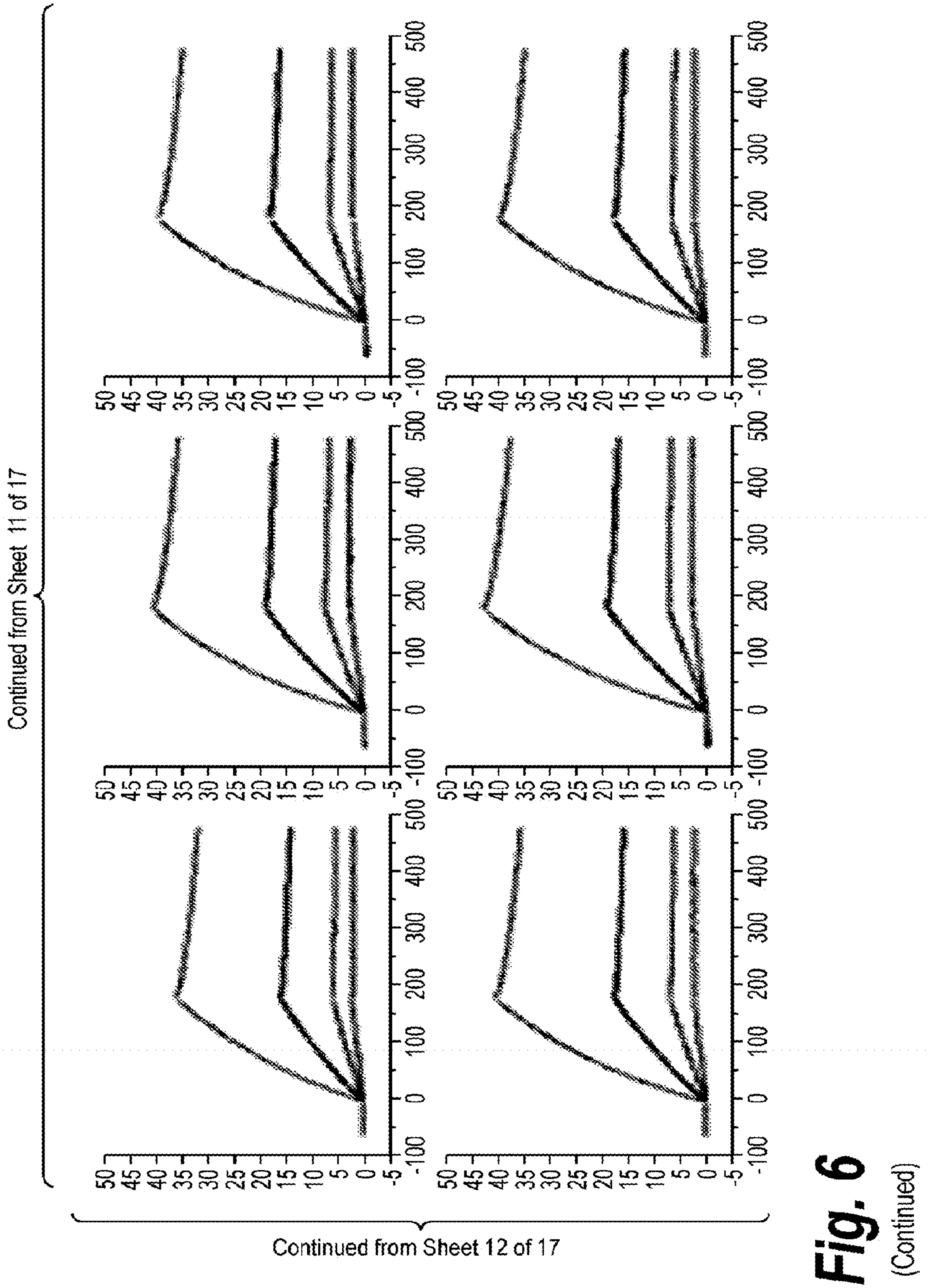

The Biacore T200 instrument was used to assess the TGFβ binding affinity of purified CAT192 WT and LC mutant Fabs. TGFβ1, TGFβ2, and TGFβ3 (124, 125, and 112 RU) were immobilized to a CMS series S chip using amine chemistry. A wide concentration range was used to account for both the low and high affinity binders. The Fabs were diluted 3-fold from 270 to 0.37 nM in HBS-EP+ buffer. Each sample was injected in duplicate. The KD was determined using the typical concentration range with 30 nM as the top concentration. The Biacore binding results were in accordance with the Octet results described above, namely, addition of amino acids in the elbow region of CAT192 LC improved the binding affinity to TGFβ1. A step-wise improvement with insertion of each additional residue was demonstrated (FIG. 6). None of the CAT192 Fab LC mutants bound to TGFβ2 or TGFβ3 under the same conditions, demonstrating that the mutants retained the isoform-selectivity, while significantly increasing TGFβ1 binding. Therefore, the elbow engineered mutants were a set of novel variants with isoform-selectivity and high affinity binding to TGFβ1.

TABLE 3

$K_D$ of Modified Fabs

| Sample | $K_D$ (nM) |
|---|---|
| WT Fab | n/a |
| LC + G Fab | n/a |
| LC + GG Fab | 3.32 |
| LC + GGS Fab | 3.76 |
| A25S Fab | n/a |

Example 2: Modified IgG4 Antibody with Additional Amino Acids in the Heavy Chain Elbow Region As a follow up to the light chain mutants in the elbow region which has shown high affinity and TGFβ1-selective binding, mutants were also designed to increase flexibility/affinity by inserting additional amino acids in the heavy chain elbow region, which linked the antibody Fv domain to the CH1 domain. More specifically, mutants were designed to add one glycine (G), two glycines (GG), and four glycines and a serine (GGGGS; SEQ ID NO: 63) sequence into the wild-type heavy chain elbow region as shown below in Table 4, with the added amino acids underlined.

TABLE 4

| Modified-IgG4 Heavy Chain Elbow Insertion Mutants | | |
|---|---|---|
| Name | Position | Amino acid sequence |
| WT | Heavy chain elbow region | TVTVSSAS (SEQ ID No. 44) |
| HC + G | Heavy chain elbow region | TVTVSGSAS (SEQ ID No. 45) |
| HC + GG | Heavy chain elbow region | TVTVSGGSAS (SEQ ID No. 46) |
| HC + GG-ST | Heavy chain elbow region | TVTVSGGSA (SEQ ID No. 47) |
| HC + GGGGS | Heavy chain elbow region | TVTVSGGGGSSAS (SEQ ID No. 48) |

The HC+GG-ST was an unexpected by-product from the PCR mutagenesis process, which added the two glycines in the elbow as designed but also had two amino acids deleted at the end of the elbow region, as confirmed by DNA sequencing. This mutant had the same number of amino acids in the heavy chain elbow region but different amino acids composition in the elbow linker. It was included as a control for characterization and affinity comparisons.

CAT192 HC + G primers
Forward
(SEQ ID No. 50)
5'-ccaccgtgacagtgtctggcagcgccagc-3'

Complement
(SEQ ID No. 51)
5'-gctggcgctgccagacactgtcacggtgg-3'

CAT192 HC + GG-ST primers
Forward
(SEQ ID No. 52)
5'-ccaccgtgacagtgtctggcggcagcgccagc-3'

Complement
(SEQ ID No. 53)
5'-gctggcgctgccgccagacactgtcacggtgg-3'

CAT192 HC + GGGGS primers
Forward
(SEQ ID No. 54)
5'-caccaccgtgacagtgtctggcggcggcggcagcagcgccagca-3'

Complement
(SEQ ID No. 55)
5'-tgctggcgctgctgccgccgccgccagacactgtcacggtggtg-3'

-continued

CAT192 HC + GG primers
Forward
(SEQ ID NO: 59)
5'-caccaccgtgacagtgtctggcggcagcgccagca-3'

Complement
(SEQ ID No. 60)
5'-tgctggcgctgccgccagacactgtcacggtggtg-3'

These CAT192 HC mutants were co-expressed with CAT192 LC Fab using the Expi293F transfection system (Life Technologies) in a 24-well plate format (4×1 mL). Conditioned media was harvested 4 days post-transfection and then purified using PureSpeed IMAC tips from Rainin in order to accurately assess the affinity to TGFβ1.

The Biacore T200 instrument was used to assess the TGFβ binding affinity of purified CAT192 mutant Fabs as described in Example 1. The results shown in FIG. 6 suggested that, like the mutants in the light chain elbow region, addition of amino acids in the elbow region of CAT192 heavy chain also improved the binding affinity to TGFβ1. For example, the CAT192 HC+GGGGS (SEQ ID NO: 63) mutant showed very high affinity binding to TGFβ1.

Example 3: Heavy and Light Chain Combination Mutants

Combination CAT192 mutants were created by co-transfection DNAs harboring mutants at the elbow regions of both heavy and light chains using the Expi293F transfection system (Life Technologies) in a 24-well plate format (4×1 mL). The different combinations are listed in Table 5.

TABLE 5

| Various Heavy and Light Chain Combination Mutants | | | | | |
|---|---|---|---|---|---|
| WT HC<br>WT LC | WT HC<br>LC + G | WT HC<br>LC + GG | WT HC<br>LC + GGS | WT HC<br>LC + GGGS<br>(SEQ ID<br>NO: 62) | WT HC<br>LC + GGGGS<br>(SEQ ID<br>NO: 63) |
| HC + G<br>WT LC | HC + G<br>LC + G | HC + G<br>LC + GG | HC + G<br>LC + GGS | HC + G<br>LC + GGGS<br>(SEQ ID<br>NO: 62) | HC + G<br>LC + GGGGS<br>(SEQ ID<br>NO: 63) |
| HC + GG<br>WT LC | HC + GG<br>LC + G | HC + GG<br>LC + GG | HC + GG<br>LC + GGS | HC + GG<br>LC + GGGS<br>(SEQ ID<br>NO: 62) | HC + GG<br>LC + GGGGS<br>(SEQ ID<br>NO: 63) |
| HC + GG-ST<br>WT LC | HC + GG-ST<br>LC + G | HC + GG-ST<br>LC + GG | HC + GG-ST<br>LC + GGS | HC + GG-ST<br>LC + GGGS<br>(SEQ ID<br>NO: 62) | HC + GG-ST<br>LC + GGGGS<br>(SEQ ID<br>NO: 63) |

TABLE 5-continued

| Various Heavy and Light Chain Combination Mutants | | | | | |
|---|---|---|---|---|---|
| HC + GGGGS (SEQ ID NO: 63) WT LC | HC + GGGGS (SEQ ID NO: 63) LC + G | HC + GGGGS (SEQ ID NO: 63) LC + GG | HC + GGGGS (SEQ ID NO: 63) LC + GGS | HC + GGGGS (SEQ ID NO: 63) LC + GGGS (SEQ ID NO: 62) | HC + GGGGS (SEQ ID NO: 63) LC + GGGGS (SEQ ID NO: 63) |

Conditioned media was harvested 4 days post-transfection and then purified using PureSpeed IMAC tips from Rainin in order to accurately assess the affinity to TGFβ1.

Figure 3:
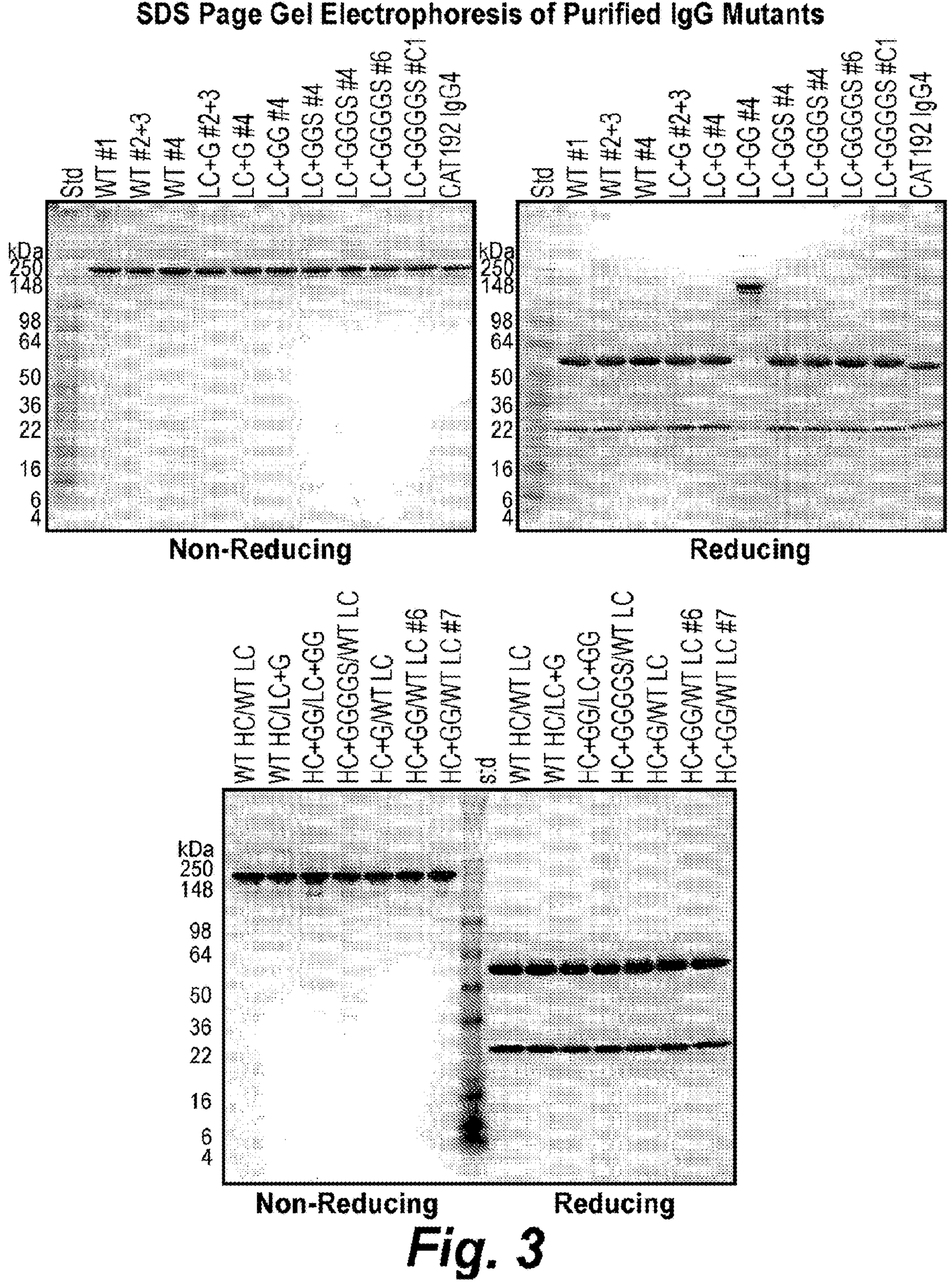
FIG. 3 shows the results of an SDS-PAGE gel of purified IgG variants with additional amino acids in the heavy and light chain elbow regions. The SDS-PAGE shows the purity of the purified IgG variants under reducing and non-reducing conditions.

The Biacore T200 instrument was used to assess the TGFβ binding affinity of purified CAT192 mutant Fabs as described in Example 1. The results shown in FIG. 3 suggested that the combination mutants restored the high affinity binding to TGFβ1 of CAT192. The binding affinity (KD) by these mutant Fabs are listed in Table 6.

TABLE 6

TGFβ1-Binding Affinity (KD) of the Heavy and Light Chain Combination Mutants Determined by Biacore

| Fabs | Antigen | $k_a$ ($\times 10^5$/Ms) | $k_d$ ($\times 10^{-4}$/s) | $K_D$ nM) |
|---|---|---|---|---|
| WT HC/WT LC | TGFβ1 | n/d | n/d | >100 |
| WT HC/LC + G | TGFβ1 | 0.16 | 10.6 | 66.5 |
| WT HC/LC + GG | TGFβ1 | 0.70 | 5.69 | 8.1 |
| WT HC/LC + GGS | TGFβ1 | 0.68 | 5.95 | 8.8 |
| WT HC/LC + GGGS (SEQ ID NO: 62) | TGFβ1 | 0.89 | 5.87 | 6.6 |
| WT HC/LC + GGGGS (SEQ ID NO: 63) | TGFβ1 | 1.18 | 5.83 | 5.0 |
| HC + G/WT LC | TGFβ1 | n/d | n/d | n/d |
| HC + G/LC + G | TGFβ1 | 1.51 | 6.32 | 4.2 |
| HC + G/LC + GG | TGFβ1 | 2.36 | 6.64 | 2.8 |
| HC + G/LC + GGS | TGFβ1 | 2.27 | 6.96 | 3.1 |
| HC + G/LC + GGGS (SEQ ID NO: 62) | TGFβ1 | 2.54 | 6.93 | 2.7 |
| HC + G/LC + GGGGS (SEQ ID NO: 63) | TGFβ1 | 2.62 | 6.90 | 2.6 |
| HC + GG/WT LC | TGFβ1 | 0.2 | 5.3 | 31.7 |
| HC + GG/LC + G | TGFβ1 | 1.1 | 4.9 | 4.4 |
| HC + GG/LC + GG | TGFβ1 | 2.2 | 3.8 | 1.8 |
| HC + GG/LC + GGS | TGFβ1 | 1.8 | 4.3 | 2.3 |
| HC + GG/LC + GGGS (SEQ ID NO: 62) | TGFβ1 | 2.4 | 3.7 | 1.5 |
| HC + GG/LC + GGGGS (SEQ ID NO: 63) | TGFβ1 | 2.2 | 3.9 | 1.8 |
| HC + GG-ST/WT LC | TGFβ1 | 0.85 | 8.11 | 9.6 |
| HC + GG-ST/LC + G | TGFβ1 | 1.31 | 5.87 | 4.5 |
| HC + GG-ST/LC + GG | TGFβ1 | 2.04 | 6.64 | 3.3 |
| HC + GG-ST/LC + GGS | TGFβ1 | 2.11 | 6.67 | 3.2 |
| HC + GG-ST/LC + GGGS | TGFβ1 | 1.47 | 6.31 | 4.3 |
| HC + GG-ST/LC + GGGGS (SEQ ID NO: 63) | TGFβ1 | 2.50 | 7.17 | 2.9 |

TABLE 6-continued

| TGFβ1-Binding Affinity (KD) of the Heavy and Light Chain Combination Mutants Determined by Biacore | | | | |
|---|---|---|---|---|
| Fabs | Antigen | $k_a$ ($\times10^5$/Ms) | $k_d$ ($\times10^{-4}$/s) | $K_D$ nM) |
| HC + GGGGS (SEQ ID NO: 63) WT LC | TGFβ1 | 0.68 | 5.79 | 8.5 |
| HC + GGGGS (SEQ ID NO: 63)/LC + G | TGFβ1 | 2.21 | 6.77 | 3.1 |
| HC + GGGGS (SEQ ID NO: 63)/LC + GG | TGFβ1 | 2.65 | 7.27 | 2.7 |
| HC + GGGGS (SEQ ID NO: 63)/LC + GGS | TGFβ1 | 2.63 | 7.09 | 2.7 |
| HC + GGGGS (SEQ ID NO: 63)/LC + GGGS | TGFβ1 | 2.78 | 7.16 | 2.6 |
| HC + GGGGS (SEQ ID NO: 63)/LC + GGGGS (SEQ ID NO: 63) | TGFβ1 | 2.64 | 7.44 | 2.8 |
| GC1008 Fab | TGFβ1 | 7.11 | 20.80 | 2.9 |

n/d = none detected

Fewer amino acids insertions were required when the elbow region of both heavy chain and light chain were engineered. For example, combination of "HC+G" and "LC+G" mutant showed very high affinity binding to TGFβ1.

Example 4: Affinity and Potency Characterization of Full Length IgG4 Variants Mutants in IgG4 format were generated to determine if the regained affinity by Biacore can be confirmed in the A549 cell-based potency assay. The CAT192 HC Fab was cloned into the heavy chain S228P IgG4 backbone to minimize the half-antibody formation, and Expi293F cells were then co-transfected with CAT192 IgG4 S228P HC and the LC insertion mutant.

Figure 4:
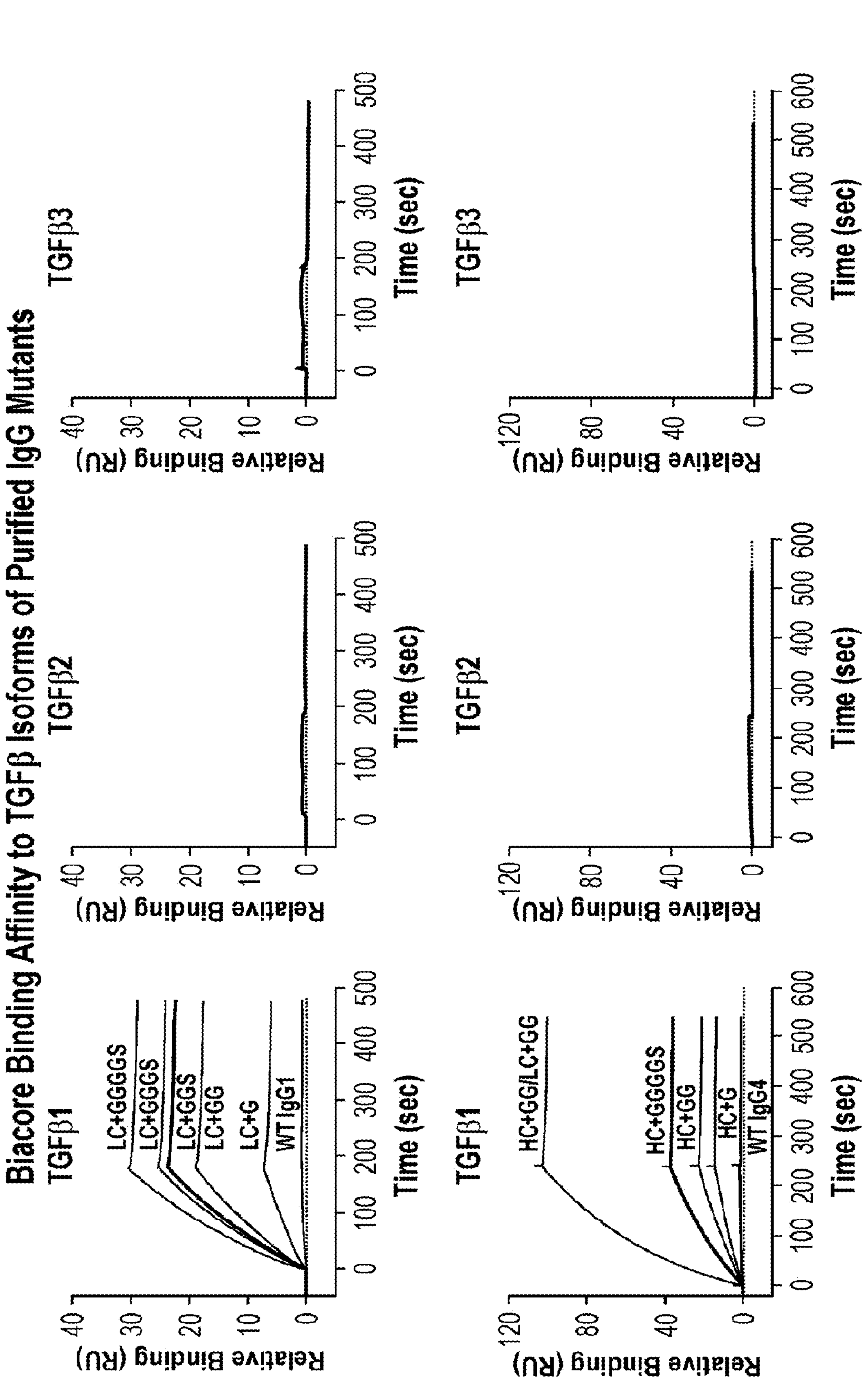
FIG. 4 shows a Biacore binding assay of purified IgG variants with additional amino acids in the heavy and light chain elbow regions. The Biacore assay result demonstrates the isoform-selective and high affinity binding by the variants.

A 30 mL transfection was performed on the full length CAT192 HC and LC insertion mutants in order to obtain enough material for the bioassay. Expi293F cells were transfected with 30 μg DNA (15 μg LC+15 μg HC). Conditioned media was collected 4 days after the transfection and analyzed by Octet using Protein A biosensors to have around 200 μg/mL expression. The CM was then purified using Hi-Trap Protein A HP columns with a peristaltic pump. CM was loaded onto each column at 0.5 mL/min, washed with 25 column volumes (CV) of 50 mM NaPi, 25 mM NaCl pH 7.1 (2 mL/min), washed with 25 CV of 10 mM sodium succinate pH 6.0 (2 mL/min), and eluted in 3×2 mL fractions with 10 mM sodium succinate pH 3.75 at 1 mL/min (labeled #1,#2,#3). The protein A eluates were neutralized with 0.2 M NaOH, and 0.2 M NaCl was added for a final concentration of 40 mM NaCl. The samples were then concentrated and buffer exchanged into 50 mM NaPi, 25 mM NaCl pH 7.1. These CAT192 IgG4 S228P HC and LC insertion mutant protein A eluates were then run on a 4-20% Tris Glycine gel (FIG. 3) and compared by Biacore for TGFβ1/TGFβ2/TGFβ3 binding (FIG. 4). Biacore results showed that the purified CAT192 IgG4 mutants indeed regained TGFβ1 binding. None of the mutants bound to TGFβ2 or TGFβ3 (FIG. 4).

TABLE 7

| TGFβ1-Binding Affinity (KD) of the Full-length IgG4 Variants as Determined by Biacore | | | |
|---|---|---|---|
| Sample | $k_a$ ($\times10^5$/Ms) | $k_d$ ($\times10^{-4}$/s) | $K_D$ (nM) |
| CAT192 IgG4 S228P | n/d | n/d | >100 |
| CAT192 IgG4 S228P LC + G | 0.15 | 5.26 | 36.1 |
| CAT192 IgG4 S228P LC + GG | 1.0 | 0.2 | 0.2 |
| CAT192 IgG4 S228P LC + GGS | 0.8 | 2.2 | 2.7 |
| CAT192 IgG4 S228P LC + GGGS (SEQ ID NO: 62) | 0.6 | 0.6 | 1.0 |
| CAT192 IgG4 S228P LC + GGGGS (SEQ ID NO: 63)) | 0.6 | 1.5 | 2.6 |
| CAT192 IgG4 S228P HC + G | 0.5 | 2.1 | 4.1 |
| CAT192 IgG4 S228P HC + GG | 1.0 | 2.0 | 2.2 |

TABLE 7-continued

| TGFβ1-Binding Affinity (KD) of the Full-length IgG4 Variants as Determined by Biacore | | | |
|---|---|---|---|
| Sample | $k_a$ ($\times10^5$/Ms) | $k_d$ ($\times10^{-4}$/s) | $K_D$ (nM) |
| CAT192 IgG4 S228P HC + GGGGS (SEQ ID NO: 63) | 1.1 | 1.5 | 1.3 |
| CAT192 IgG4 S228P HC + GG/LC + GG | 2.4 | 0.5 | 0.2 |

n/d =none detected

Figure 5:
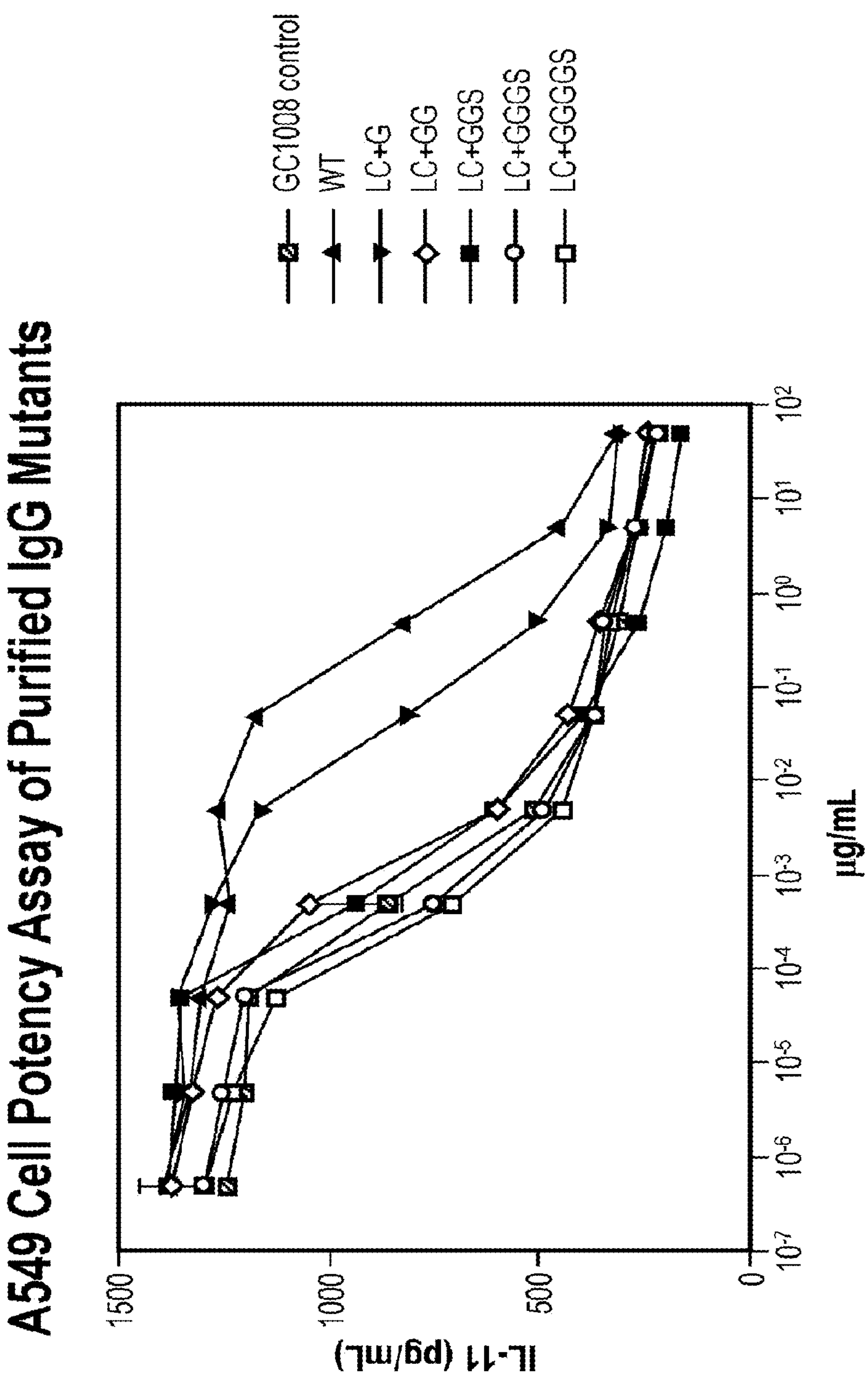
FIG. 5 shows an A549 cell bioassay of purified IgG variants with additional amino acids in the light chain elbow regions. The A549 assay compares the inhibitory effects by various antibody constructs on TGFβ1-stimulated IL-11 production, showing the elbow engineered variants are highly potent in this cell-based potency assay.

The CAT192 IgG S228P LC insertion mutants were then characterized in a A549 cell potency assay (Rapoza et al., 2006, J Immunol Methods, Vo 316, pp 18). The results (FIG. 5) showed that the CAT192 insertion mutants neutralized TGFβ1 activity, as demonstrated by the inhibitory effects by the mutants on TGFβ1-stimulated IL-11 production. It appeared that two glycines added to the light chain elbow were sufficient to for CAT192 to regain efficacy, as observed in the Biacore binding experiment.

Example 5: Thermostability Study

Figure 7:
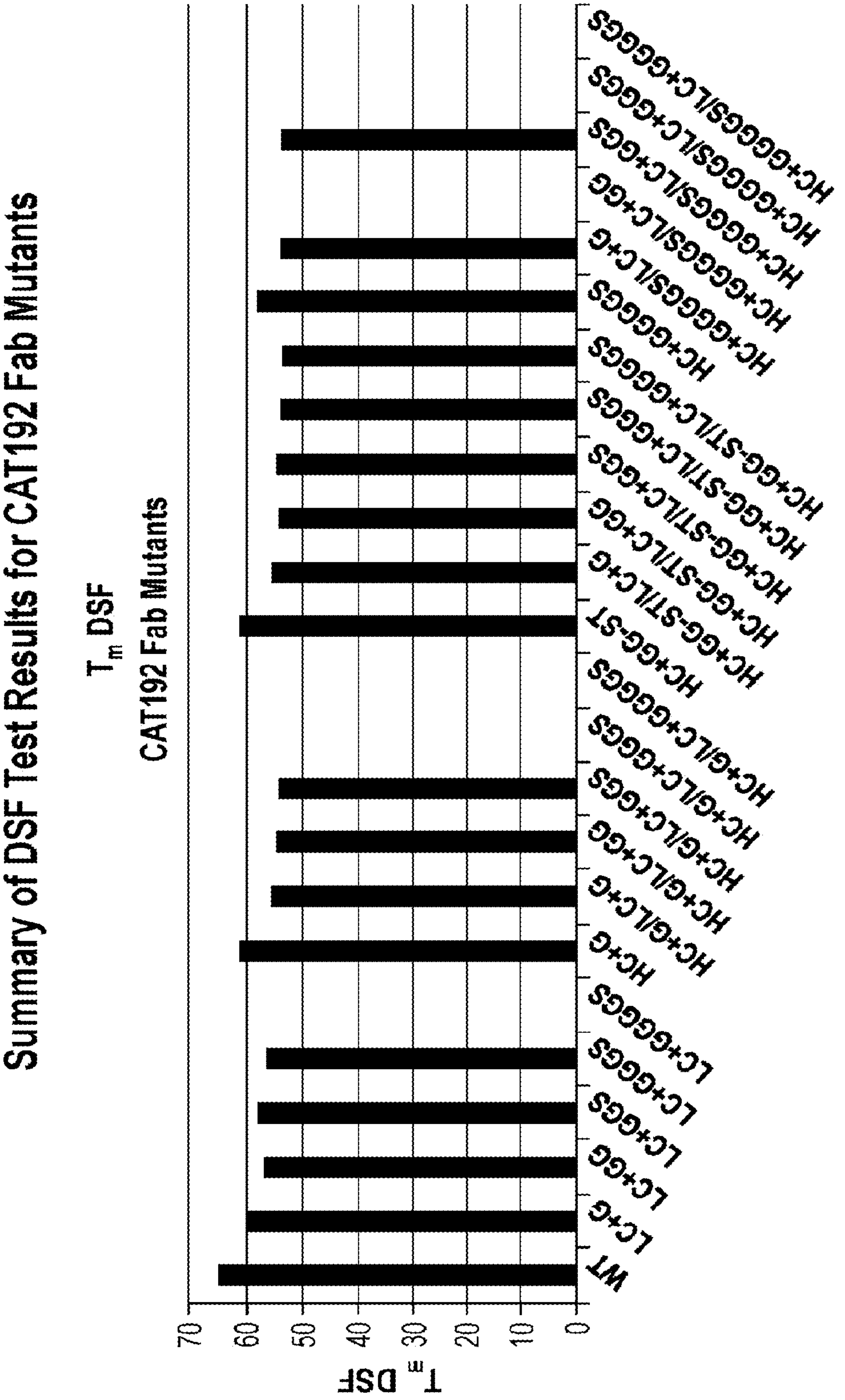
FIG. 7 shows results of a Differential Scanning Fluorimetry (DSF) analysis of the thermostability of the CAT192 Fab mutants.
Figure 8:
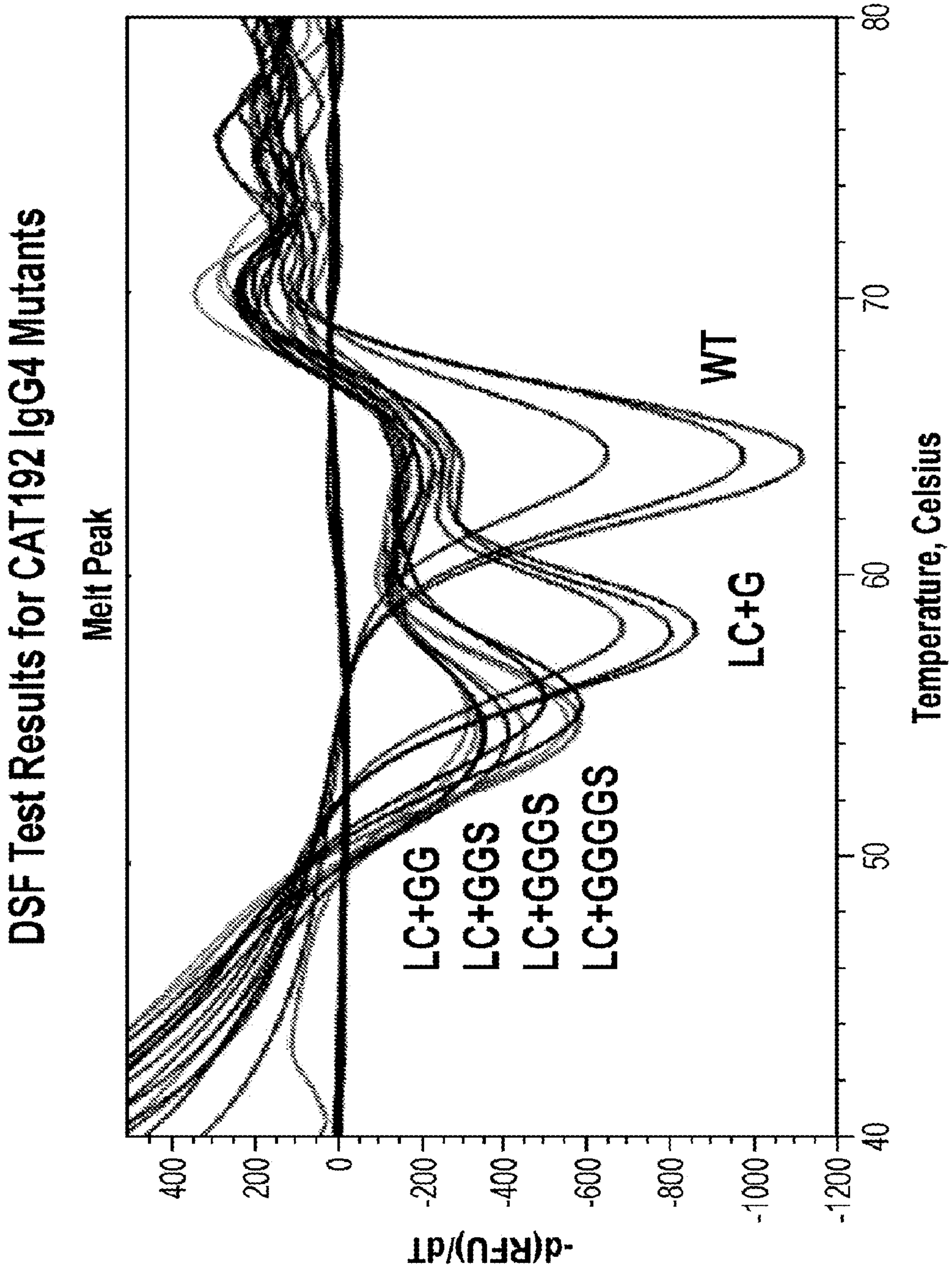
FIG. 8 shows results of a Differential Scanning Fluorimetry (DSF) analysis of the thermostability of the CAT192 IgG4 mutants.

Differential Scanning Fluorimetry (DSF) was performed on the elbow-insertion mutants to determine how the additional amino acids at the hinge region of heavy chain and light chain affected the thermostability of the CAT192 Fab insertion mutants. The basic principle of DSF is that as the temperature increases, a fluorescent dye binds to the hydrophobic regions of the protein as it unfolds providing an increase in signal. This method can be performed with limited sample and can be used to get relative stability of samples in a high throughput manner. Sypro orange was used as the fluorescent dye. The conditions used were 0.1 mg/mL protein, a 1:4000 dye ratio and a total volume of 10 μL. The results showed that relative stability of the CAT192 Fab insertion mutants decreased slightly with the addition of glycines in the elbow, with the least stable mutants having the longest addition (FIG. 7). The Tm values are summarized in FIG. 7. The Tm values of some of the longer chain mutants were not calculated due to their unfolding pattern. The slight decrease was also observed when some of the light chain mutants were converted from Fab into IgG4 format (FIG. 8).

Example 6: Crystal Structure Determination of CAT192 Fab Variants

The protein structures of CAT192 Fab WT and 3 variants were solved to provide the structural explanation as to how the high affinity was restored with the increased flexibility of the variable domains.

A 150 mL transfection was performed on the CAT192 HC and LC Fab insertion mutants to obtain enough material for the structure studies. Expi293F cells were transfected with 150 μg DNA (75 μg LC+75 μg HC). Conditioned media was collected 5 days after the transfection. The CM was then purified using His-Trap Excel columns equilibrated with 20 mM NaPi pH 7.4, 500 mM NaCl, 5 mM imidazole. Fab protein was eluted with 20 mM NaPi pH 7.4, 500 mM NaCl, 500 mM imidazole and immediately buffer exchanged into 20 mM HEPES pH 7.0, 50 mM NaCl using a size exclusion chromatography column (Superdex 200 10/300). The Fabs were then concentrated to 20 mg/mL and sparse matrix screens were set-up at both room temperature and 4° C. All crystals used for structure determination were obtained at 4° C. in a 1:1 protein to crystallization condition ratio. Wild-type protein and the lower binding affinity mutants crystallized in a P21 space group in similar PEG conditions (WT: 12% PEG 8K/0.1 M sodium cacodylate pH 6/0.2 M $MgCl_2$, CAT192 WT HC/LC+G: 12% PEG 20K/0.1 M MES pH 6.5, CAT192 HC+GGGGS (SEQ ID NO: 63)/WT LC: 12% PEG 20K, 0.1 M MES pH 5.75). The high binding affinity mutant (HC+GG/LC+GG) crystallized in 2 M ammonium sulfate, 0.1 M sodium acetate pH 4.6 (space group: C2).

Figure 9:
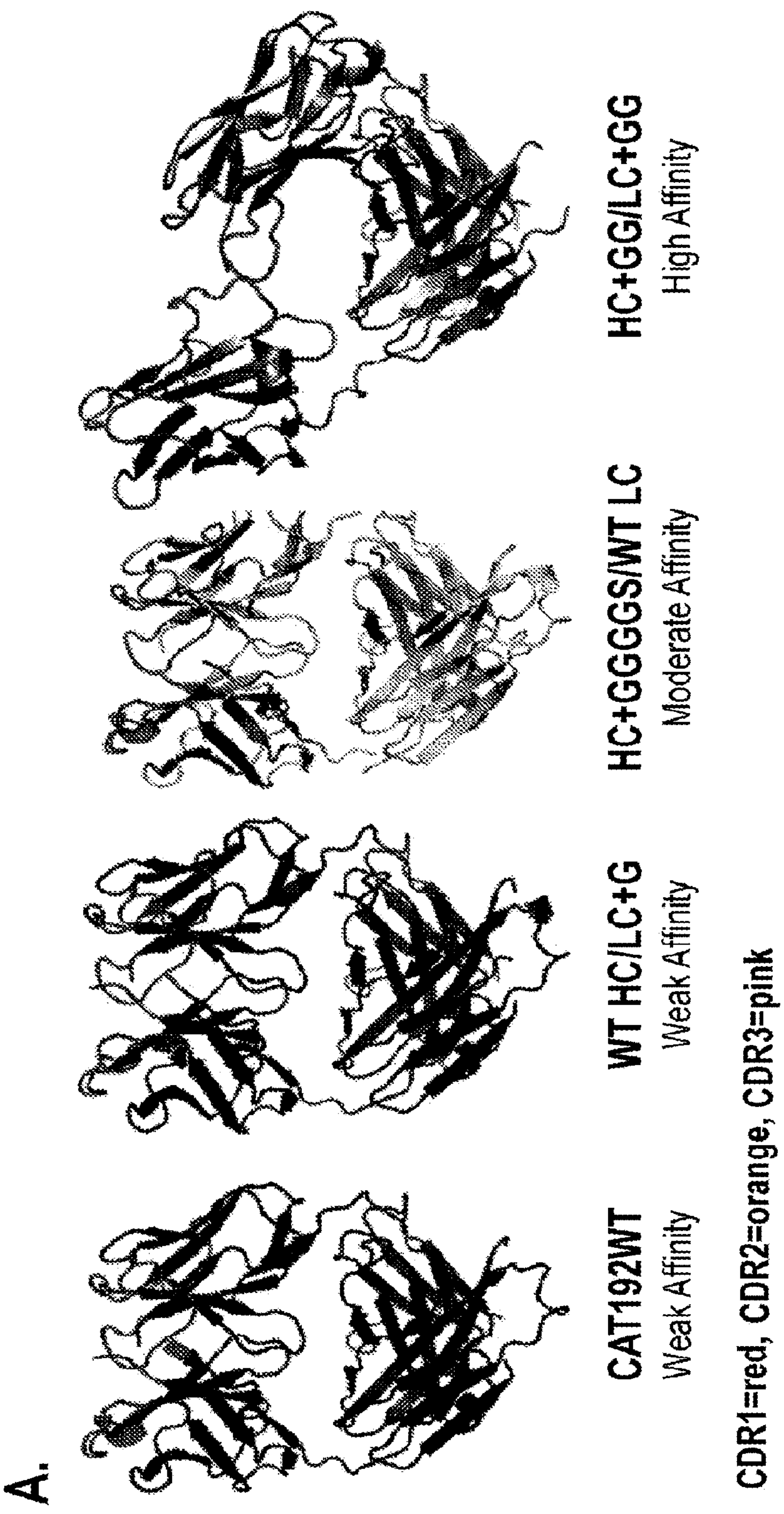
FIG. 9 shows the crystal structures solved for the CAT192 Fab variants.
Figure 9:
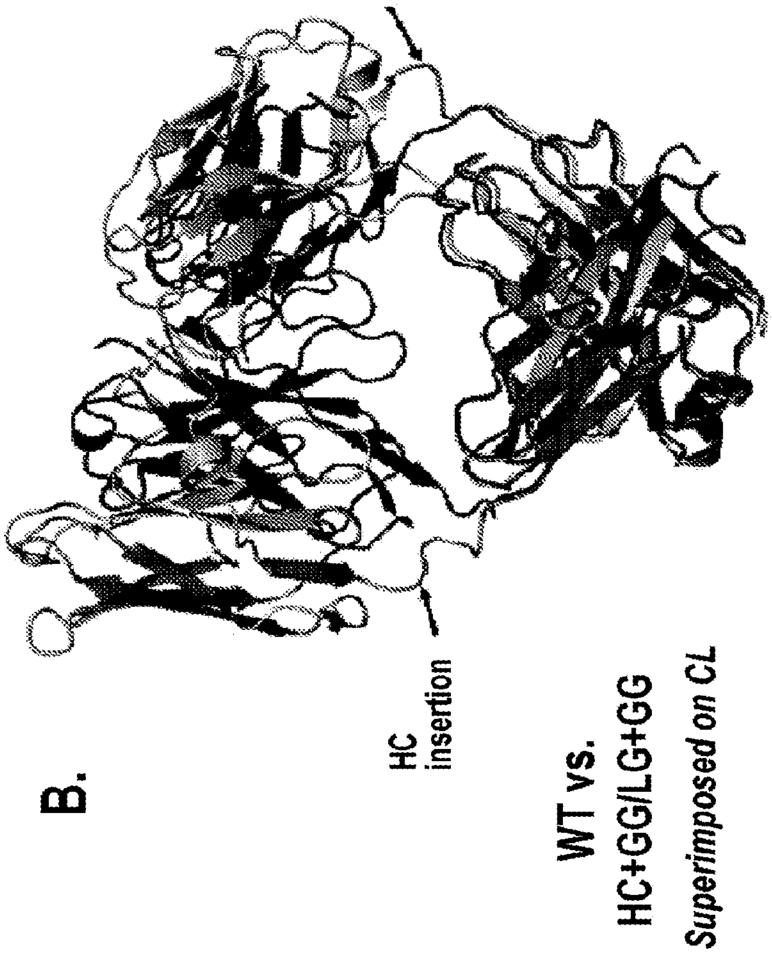

The low/moderate binding affinity variants and the wild type Fab structures (HC+WT/LC+G and HC+GGGGS (SEQ ID NO: 63)/LC+WT) were nearly identical (FIG. 9, part A). WT HC/LC+G and HC+GGGGS(SEQ ID NO: 63)/WT LC superimposed with WT CAT192 with a R.M.S.D of 0.516 Å and 0.538 Å respectively. In each of these structures, the electron density for the CDRH3 region was missing for all molecules in the asymmetric unit. This implied that this CDR was highly flexible for the low/moderate binding affinity mutants. In contrast, the high binding affinity mutant (HC+GG/LC+GG) displayed large conformational changes in the variable domains compared to the other CAT192 Fab structures (FIG. 9, part A). While the constant domains between all four Fabs superimposed nicely, the variable domains in CAT192 HC+GG/LC+GG shifted significantly compared to the other structures (FIG. 9, part B). Furthermore, the HC CDR3 region was completely structured in the high binding affinity structure and was stabilized by interacting with the LC CDR3 (<3 Å). These four structures, in accordance with the Biacore results, suggested that large conformational rearrangement was required to restore the high binding affinity of CAT192.

SEQUENCE LISTING

SEQ ID No. 1: Human IgG1 VH domain Clone SL15 (SQN4 U.S. Pat. No. 6,492,497)
EVQLVESGGGVVQPGRSLRLSCAASGFTFSSYGMHWVRQAPGKELEWVAVI

SYDGSIKYYADSVKGRFTISRDNSKNTLYLQMNSLRAEDTAVYYCARTGEYS

GYDTDPQYSWGQGTTVTVSS

SEQ ID No. 2: Human IgG1 VH domain Clone JT182 (SQN10 U.S. Pat. No. 6,492,497)
QVQLVESGGGVVQPGRSLRLSCAASGFTFSSYGMHWVRQAPGKELEWVAVI -continued

SYDGSIKYYADSVKGRFTISRDNSKNTLYLQMNSLRAEDTAVYYCARTGEYS

GYDTPASPDWGQGTTVTVSS

SEQ ID No. 3: Human IgGI Vκ domain Clone SL15A: (SQN6 U.S. Pat. No. 6,492,497)
EIVLTQSPSSLSASVGDRVTITCRASQGIGDDLGWYQQKPGKAPILLTYGTSTL

QSGVPSRFSGSGSGTDFTLTINSLQPEDFATYYCLQDSNYPLTFGGGTRLEIK

SEQ ID No. 4: Human IgGI Vκ domain Clone SL15S: (SQN8 U.S. Pat. No. 6,492,497)
EIVLTQSPSSLSASVGDRVTITCRSSQGIGDDLGWYQQKPGKAPILLTYGTSTL

QSGVPSRFSGSGSGTDFTLTINSLQPEDFATYYCLQDSNYPLTFGGGTRLEIK

SEQ ID No. 5: Human IgG1 Hinge Region
PKSCDKTHTCPPCPAPELLGGP

SEQ ID No. 6: Human IgG1 Fc Region
SVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSLSPGK

SEQ ID No. 7
SYGMH

SEQ ID No. 8
VISYDGSIKYYADSVKG

SEQ ID No. 9
TGEYSGYDTSGVEL

SEQ ID No. 10
TGEYSGYDTDPQYS

SEQ ID No. 11
TGFYSGYDTPASPD

SEQ ID No. 12
RASQGIGDDLG

SEQ ID No. 13
GTSTLQS

SEQ ID No. 14
LQDSNYPLT

SEQ ID No. 15
$TGX_1YSGYDTX_2X_3X_4X_5X_6$

SEQ ID No. 16: CAT192 (IgG4) Light Chain
EWLTQSPSSLSASVGDRVTITCRASQGIGDDLGWYQQKPGKAPILLIYGTSTL

QSGVPSRFSGSGSGTDFTLTINSLQPEDFATYYCLQDSNYPLTFGGGTRLEIKR

TVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGE

C

SEQ ID No. 17: CAT192 (IgG4) Heavy Chain
EVQLVESGGGVVQPGRSLRLSCAASGFTFSSYGMHWVRQAPGKELEWVAVI

SYDGSIKYYADSVKGRFTISRDNSKNTLYLQMNSLRAEDTAVYYCARTGEYS

GYDTDPQYSWGQGTTVTVSSASTKGPSVFPLAPCSRSTSESTAALGCLVKDYF

PEPVTVSWNSGALTSGVHTFPAVLQSSGLYSLSSVVTVPSSSLGTKTYTCNVD

HKPSNTKVDKRVESKYGPPCPSCPAPEFLGGPSVFLFPPKPKDTLMISRTPEVT

CVVVDVSQEDPEVQFNWYVDGVEVHNAKTKPREEQFNSTYRVVSVLTVLHQ

DWLNGKEYKCKVSNKGLPSSIEKTISKAKGQPREPQVYTLPPSQEEMTKNQV

-continued

SLTCLVKGFYPSDIAVEWESNGQPENNYKTTPPVLDSDGSFFLYSRLTVDKSR

WQEGNVFSCSVMHEALHNHYTQKSLSLSLGK

SEQ ID No. 18: CAT192 (IgG4) S228P Heavy Chain
EVQLVESGGGVVQPGRSLRLSCAASGFTFSSYGMHWVRQAPGKELEWVAVI

SYDGSIKYYADSVKGRFTISRDNSKNTLYLQMNSLRAEDTAVYYCARTGEYS

GYDTDPQYSWGQGTTVTVSSASTKGPSVFPLAPCSRSTSESTAALGCLVKDYF

PEPVTVSWNSGALTSGVHTFPAVLQSSGLYSLSSVVTVPSSSLGTKTYTCNVD

HKPSNTKVDKRVESKYGPPCPPCPAPEFLGGPSVFLFPPKPKDTLMISRTPEVT

CVVVDVSQEDPEVQFNWYVDGVEVHNAKTKPREEQFNSTYRVVSVLTVLHQ

DWLNGKEYKCKVSNKGLPSSIEKTISKAKGQPREPQVYTLPPSQEEMTKNQV

SLTCLVKGFYPSDIAVEWESNGQPENNYKTTPPVLDSDGSFFLYSRLTVDKSR

WQEGNVFSCSVMHEALHNHYTQKSLSLSLGK

SEQ ID No. 19: CAT191 (scFv)
EVQLVESGGGVVQPGRSLRLSCAASGFTFSSYGMHWVRQAPGKELEWVAVI

SYDGSIKYYADSVKGRFTISRDNSKNTLYLQMNSLRAEDTAVYYCARTGEYS

GYDTDPQYSWGQGTTVTVSSSGGGSGGGGSGGGGSEIVLTQSPSSLSASVGD

RVTITCRSSQGIGDDLGWYQQKPGKAPILLIYGTSTLQSGVPSRFSGSGSGTDF

TLTINSLQPEDFATYYCLQDSNYPLTFGGGTRLEIK

SEQ ID No. 20: Human TGFβ1
ALDTNYCFSSTEKNCCVRQLYIDFRKDLGWKWIHEPKGYHANFCLGPCPYIW

SLDTQYSKVLALYNQHNPGASAAPCCVPQALEPLPIVYYVGRKPKVEQLSNM

IVRSCKCS

SEQ ID No. 21: CAT192 IgG4 Wild-type LC Elbow Region
LEIKRTVA

SEQ ID No. 22: Mutant LC Elbow Region with 1 Additional Amino Acid Inserted
LEIKGRTVA SEQ ID No. 23: Mutant LC Elbow Region with 2 Additional Amino Acids Inserted
LEIKGGRTVA SEQ ID No. 24: Mutant LC Elbow Region with 3 Additional Amino Acids Inserted
LEIKGGSRTVA SEQ ID No. 25: Mutant LC Elbow Region with 4 Additional Amino Acids Inserted
LEIKGGGSRTVA SEQ ID No. 26: Mutant LC Elbow Region with 5 Additional Amino Acids Inserted
LEIKGGGGSRTVA SEQ ID No. 27: Coding sequence of CAT192 (IgG1) Light Chain
atgggctggtcctgcatcatcctgtttctggtggccacagccaccggcgtgcacagcGAGATCGTGCTGACA

CAGAGCCCCAGCAGCCTGTCTGCCAGCGTGGGCGACAGAGTGACCATCAC

CTGTAGAGCCAGCCAGGGCATCGGCGACGACCTGGGATGGTATCAGCAGA

AGCCTGGCAAGGCCCCCATCCTGCTGATCTACGGCACCAGCACACTGCAG

AGCGGCGTGCCCTCCAGATTTTCTGGCAGCGGCTCCGGCACCGACTTCACC

CTGACCATCAACAGCCTGCAGCCCGAGGACTTCGCCACCTACTACTGTCTG

CAAGACAGCAACTACCCCCTGACCTTCGGCGGAGGCACCCGGCTGGAAAT

CAAGCGTACGGTGGCCGCTCCTTCCGTGTTCATCTTCCCTCCCTCCGACGA

-continued

GCAGCTGAAGTCCGGCACCGCCTCCGTGGTGTGTCTGCTGAACAACTTCTA

CCCTCGGGAGGCCAAGGTGCAGTGGAAGGTGGACAACGCCCTGCAGTCCG

GCAACTCCCAGGAGTCCGTCACCGAGCAGGACTCCAAGGACAGCACCTAC

TCCCTGTCCTCCACCCTGACCCTGTCCAAGGCCGACTACGAGAAGCACAA

GGTGTACGCCTGTGAGGTGACCCACCAGGGCCTGTCCAGCCCTGTGACCA

AGTCCTTCAACCGGGGCGAGTGCTGA

SEQ ID No. 28: CAT192LC + G (LEIKGRTVA), Forward
5'-ggctggaaatcaagggccgtacggtggccgc-3'

SEQ ID No. 29: CAT192LC + G (LEIKGRTVA), Complement
5'-gcggccaccgtacggcccttgatttccagcc-3'

SEQ ID No. 30: CAT192LC + GG (LEIKGGRTVA), Forward
5'-ggctggaaatcaagggcggccgtacggtggccgc-3'

SEQ ID No. 31: CAT192LC + GG (LEIKGGRTVA), Complement
5'-gcggccaccgtacggccgcccttgatttccagcc-3'

SEQ ID No. 32: CAT192LC + GGS (LEIKGGSRTVA), Forward
5'-ggctggaaatcaagggcggcagccgtacggtggccgc-3'

SEQ ID No. 33: CAT192LC + GGS (LEIKGGSRTVA), Complement
5'-gcggccaccgtacggctgccgcccttgatttccagcc-3'

SEQ ID No. 34: CAT192LC + GGGS (LEIKGGGSRTVA), Forward
5'-ggctggaaatcaagggcggcggcagccgtacggtggccgc-3'

SEQ ID No. 35: CAT192LC + GGGS (LEIKGGGSRTVA), Complement
5'-gcggccaccgtacggctgccgccgcccttgatttccagcc-3'

SEQ ID No. 36: CAT192LC + GGGGS (LEIKGGGGSRTVA), Forward
5'-ggctggaaatcaagggcggcggcggcagccgtacggtggccgc-3'

SEQ ID No. 37: CAT192LC + GGGGS (LEIKGGGGSRTVA), Complement
5'-gcggccaccgtacggctgccgccgccgcccttgatttccagcc-3'

SEQ ID No. 38: CAT192 IgG1 Wild-Type LC
EIVLTQSPSSLSASVGDRVTITCRASQGIGDDLGWYQQKPGKAPILLIYGTSTL

QSGVPSRFSGSGSGTDFTLTINSLQPEDFATYYCLQDSNYPLTFGGGTRLEIKR

TVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGE

C

SEQ ID No. 39: Mutant Light Chain with 1 Additional Amino Acid Inserted
EIVLTQSPSSLSASVGDRVTITCRASQGIGDDLGWYQQKPGKAPILLIYGTSTL

QSGVPSRFSGSGSGTDFTLTINSLQPEDFATYYCLQDSNYPLTFGGGTRLEIKG

RTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRG

EC

SEQ ID No. 40: Mutant Light Chain with 2 Additional Amino Acids Inserted
EIVLTQSPSSLSASVGDRVTITCRASQGIGDDLGWYQQKPGKAPILLIYGTSTL

QSGVPSRFSGSGSGTDFTLTINSLQPEDFATYYCLQDSNYPLTFGGGTRLEIKG

GRTVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKSFNR

GEC

SEQ ID No. 41: Mutant Light Chain with 3 Additional Amino Acids Inserted
EIVLTQSPSSLSASVGDRVTITCRASQGIGDDLGWYQQKPGKAPILLIYGTSTL

QSGVPSRFSGSGSGTDFTLTINSLQPEDFATYYCLQDSNYPLTFGGGTRLEIKG

-continued

GSRTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTKSFN

RGEC

SEQ ID No. 42: Mutant Light Chain with 4 Additional Amino Acids Inserted
EIVLTQSPSSLSASVGDRVTITCRASQGIGDDLGWYQQKPGKAPILLIYGTSTL

QSGVPSRFSGSGSGTDFTLTINSLQPEDFATYYCLQDSNYPLTFGGGTRLEIKG

GGSRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSF

NRGEC

SEQ ID No. 43: Mutant Light Chain with 5 Additional Amino Acids Inserted
EIVLTQSPSSLSASVGDRVTITCRASQGIGDDLGWYQQKPGKAPILLIYGTSTL

QSGVPSRFSGSGSGTDFTLTINSLQPEDFATYYCLQDSNYPLTFGGGTRLEIKG

GGGSRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKS

FNRGEC

SEQ ID No. 44: CAT192 IgG4 Wild-Type HC Elbow Region
TVTVSSAS

SEQ ID No. 45: Mutant HC Elbow Region with 1 Additional Amino Acid Inserted
TVTVSGSAS SEQ ID No. 46: Mutant HC Elbow Region with 2 Additional Amino Acids Inserted
TVTVSGGSAS SEQ ID No. 47: Mutant HC Elbow Region with 2 Additional Amino Acids Inserted and one Amino Acid Deleted
TVTVSGGSA SEQ ID No. 48: Mutant HC Elbow Region with 5 Additional Amino Acids Inserted
TVTVSGGGGSSAS SEQ ID No. 49: Coding Sequence of CAT192 IgG4 Wild-Type HC
ATGGGCTGGTCCTGCATCATCCTGTTTCTGGTGGCCACCGCCACCGGCGTG

CACTCTGAAGTGCAGCTGGTGGAATCTGGCGGCGGAGTGGTGCAGCCTGG

CAGAAGCCTGAGACTGAGCTGTGCCGCCAGCGGCTTCACCTTCAGCAGCT

ACGGAATGCACTGGGTGCGCCAGGCCCCTGGCAAAGAACTGGAATGGGT

GGCCGTGATCAGCTACGACGGCAGCATCAAGTACTACGCCGACAGCGTGA

AGGGCCGGTTCACCATCTCCCGGGACAACAGCAAGAACACCCTGTACCTG

CAGATGAACAGCCTGCGGGCCGAGGACACCGCCGTGTACTACTGTGCTAG

AACCGGCGAGTACAGCGGCTACGACACCGACCCTCAGTACTCTTGGGGCC

AGGGCACCACCGTGACAGTGTCTAGCGCCAGCACCAAGGGCCCAAGCGTG

TTCCCTCTGGCCCCTTGCAGCAGAAGCACCAGCGAATCTACAGCCGCCCT

GGGCTGCCTCGTGAAGGACTACTTTCCCGAGCCCGTGACAGTGTCCTGGA

ACTCTGGCGCCCTGACCAGCGGAGTGCATACCTTTCCAGCCGTGCTGCAG

AGCAGCGGCCTGTACTCTCTGAGCAGCGTCGTGACTGTGCCCAGCAGCTC

TCTGGGCACCAAGACCTACACCTGTAACGTGGACCACAAGCCCAGCAACA

CCAAGGTGGACAAGAGAGTGCATCACCACCACCATCAC

-continued

SEQ ID No. 50: CAT192HC + G (TVTVSGSAS), Forward
5'-ccaccgtgacagtgtctggcagcgccagc-3'

SEQ ID No. 51: CAT192HC + G (TVTVSGSAS), Complement
5'-gctggcgctgccagacactgtcacggtgg-3'

SEQ ID No. 52: CAT192HC + GG-ST (TVTVSGGSA), Forward
5'-ccaccgtgacagtgtctggcggcagcgccagc-3'

SEQ ID No. 53: CAT192HC + GG-ST (TVTVSGGSA), Complement
5'-gctggcgctgccgccagacactgtcacggtgg-3'

SEQ ID No. 54: CAT192HC + GGGGS (TVTVSGGGGSSAS), Forward
5'-caccaccgtgacagtgtctggcggcggcggcagcagcgccagca-3'

SEQ ID No. 55: CAT192HC + GGGGS (TVTVSGGGGSSAS), Complement
5'-tgctggcgctgctgccgccgccgccagacactgtcacggtggtg-3'

SEQ ID No. 56: Mutant Heavy Chain with 1 Additional Amino Acid Inserted
EVQLVESGGGVVQPGRSLRLSCAASGFTFSSYGMHWVRQAPGKELEWVAVI

SYDGSIKYYADSVKGRFTISRDNSKNTLYLQMNSLRAEDTAVYYCARTGEYS

GYDTDPQYSWGQGTTVTVSGSASTKGPSVFPLAPSSKSTSGGTAALGCLVKD

YFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISR

TPEVTCVVVDVSHEDPEVKFNVVYVDGVEVHNAKTKPREEQYNSTYRVVSVL

TVLHQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSKLTV

DKSRWQQGNVFSCSVMHEALHNHYTQKSLSLSPGK

SEQ ID No. 57: Mutant Heavy Chain with 2 Additional Amino Acids Inserted and 2 Amino Acids Deleted
EVQLVESGGGVVQPGRSLRLSCAASGFTFSSYGMHWVRQAPGKELEWVAVI

SYDGSIKYYADSVKGRFTISRDNSKNTLYLQMNSLRAEDTAVYYCARTGEYS

GYDTDPQYSWGQGTTVTVSGGSAKGPSVFPLAPSSKSTSGGTAALGCLVKDY

FPEPVTVSWNSGALTSGVHTFPAVLQSSGLYSLSSVVTVPSSSLGTQTYICNVN

HKPSNTKVDKKVEPKSCDKTHTCPPCPAPELLGGPSVFLFPPKPKDTLMISRTP

EVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSKLTV

DKSRWQQGNVFSCSVMHEALHNHYTQKSLSLSPGK

SEQ ID No. 58: Mutant Heavy Chain with 5 Additional Amino Acids Inserted
EVQLVESGGGVVQPGRSLRLSCAASGFTFSSYGMHWVRQAPGKELEWVAVI

SYDGSIKYYADSVKGRFTISRDNSKNTLYLQMNSLRAEDTAVYYCARTGEYS

GYDTDPQYSWGQGTTVTVSGGGGSSASTKGPSVFPLAPSSKSTSGGTAALGC

LVKDYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKPKDT

LMISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTLPP

SRDELTKNQVSLTCLVKGFYPSDIAVEWESNGQPENNYKTTPPVLDSDGSFFL

YSKLTVDKSRWQQGNVFSCSVMHEALHNHYTQKSLSLSPGK

-continued

SEQ ID No. 59: CAT192HC + GG (TVTVSGGSAS), Forward
5'- caccaccgtgacagtgtctggcggcagcgccagca-3'

SEQ ID No. 60: CAT192HC + GG (TVTVSGGSAS), Complement
5'- tgctggcgctgccgccagacactgtcacggtggtg-3'

SEQ ID No. 61: Mutant Heavy Chain with 2 Additional Amino Acids Inserted
EVQLVESGGGVVQPGRSLRLSCAASGFTFSSYGMHWVRQAPGKELEWVAVI

SYDGSIKYYADSVKGRFTISRDNSKNTLYLQMNSLRAEDTAVYYCARTGEYS

GYDTDPQYSWGQGTTVTVSGGSASTKGPSVFPLAPSSKSTSGGTAALGCLVK

DYFPEPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFLYSKLT

VDKSRWQQGNVFSCSVMHEALHNHYTQKSLSLSPGK

SEQ ID No. 62: GGGS

SEQ ID No. 63: GGGGS

---

The invention claimed is:

1. An isolated polynucleotide encoding an isolated binding protein hat binds TGFβ1, or a TGFβ1-binding fragment thereof, wherein the isolated binding protein comprises (i) an immunoglobulin heavy chain (HC) having a variable domain (VH) amino acid sequence set forth in SEQ ID NO: 1, and (ii) an immunoglobulin light chain (LC) having a variable domain (VL) amino acid sequence set forth in SEQ ID NO: 3, wherein (a) the HC comprises an elbow region comprising a first linker, or (b) the LC comprises an elbow region comprising a second linker, or (c) both (a) and (b), wherein the first and second linkers independently are one to five amino acids in length and comprise G, GG, GGS, GGGS (SEQ ID NO: 62), or GGGGS (SEQ ID NO: 63).

2. The isolated polynucleotide of claim 1, wherein the HC is of a human IgG4 isotype.

3. The isolated polynucleotide of claim 2, wherein the HC comprises a hinge region comprising an S228P mutation (EU numbering).

4. The isolated polynucleotide of claim 1, wherein the HC is of a human IgG1 isotype.

5. The isolated polynucleotide of claim 1, wherein the HC comprises SEQ ID NO: 56, 57, 58, or 61.

6. The isolated polynucleotide of claim 5, wherein the LC comprises any one of SEQ ID NOs: 16 and 38-43.

7. The isolated polynucleotide of claim 1, wherein the LC comprises any one of SEQ ID NOs: 39-43.

8. The isolated polynucleotide of claim 7, wherein the HC comprises any one of SEQ ID NOs: 17, 18, 56-58, and 61.

9. An isolated polynucleotide encoding an isolated binding protein that binds TGFβ1, or a TGFβ1-binding fragment thereof, wherein the isolated binding protein comprises an immunoglobulin heavy chain and an immunoglobulin light chain comprising:

SEQ ID NOs: 18 and 39, respectively;
SEQ ID NOs: 18 and 40, respectively;
SEQ ID NOs: 18 and 41, respectively;
SEQ ID NOs: 18 and 42, respectively;
SEQ ID NOs: 18 and 43, respectively;
SEQ ID NOs: 56 and 16, respectively;
SEQ ID NOs: 56 and 38, respectively;
SEQ ID NOs: 56 and 39, respectively;
SEQ ID NOs: 56 and 40, respectively;
SEQ ID NOs: 56 and 41, respectively;
SEQ ID NOs: 56 and 42, respectively;
SEQ ID NOs: 56 and 43, respectively;
SEQ ID NOs: 57 and 16, respectively;
SEQ ID NOs: 57 and 38, respectively;
SEQ ID NOs: 57 and 39, respectively;
SEQ ID NOs: 57 and 40, respectively;
SEQ ID NOs: 57 and 41, respectively;
SEQ ID NOs: 57 and 42, respectively;
SEQ ID NOs: 57 and 43, respectively;
SEQ ID NOs: 58 and 16, respectively;
SEQ ID NOs: 58 and 38, respectively;
SEQ ID NOs: 58 and 39, respectively;
SEQ ID NOs: 58 and 40, respectively;
SEQ ID NOs: 58 and 41, respectively;
SEQ ID NOs: 58 and 42, respectively;
SEQ ID NOs: 58 and 43, respectively;
SEQ ID NOs: 61 and 16, respectively;
SEQ ID NOs: 61 and 38, respectively;
SEQ ID NOs: 61 and 39, respectively;
SEQ ID NOs: 61 and 40, respectively;
SEQ ID NOs: 61 and 41, respectively;
SEQ ID NOs: 61 and 42, respectively; or SEQ ID NOs: 61 and 43, respectively.

10. A vector comprising the polynucleotide of claim 1.

11. A host cell comprising the vector of claim 10.

* * * * *